United States Patent
Wedemeyer

(10) Patent No.: US 8,464,709 B2
(45) Date of Patent: Jun. 18, 2013

(54) CHEEK PATH AIRWAY AND CHEEK POUCH ANCHOR

(76) Inventor: Lowell R. Wedemeyer, Los Angeles County, CA (US)

(*) Notice: Subject to any disclaimer, the term of this patent is extended or adjusted under 35 U.S.C. 154(b) by 2032 days.

(21) Appl. No.: 10/714,694

(22) Filed: Nov. 17, 2003

(65) Prior Publication Data

US 2005/0103331 A1    May 19, 2005

(51) Int. Cl.
| | |
|---|---|
| A61M 15/00 | (2006.01) |
| A61M 16/00 | (2006.01) |
| A62B 7/00 | (2006.01) |
| A62B 9/00 | (2006.01) |
| A62B 18/00 | (2006.01) |
| A61F 5/56 | (2006.01) |
| A61F 11/00 | (2006.01) |
| A61C 5/14 | (2006.01) |
| A61C 3/00 | (2006.01) |
| A61C 5/00 | (2006.01) |

(52) U.S. Cl.
USPC ............ 128/200.26; 128/200.24; 128/207.14; 128/848; 128/857; 128/859; 128/860; 433/10; 433/11; 433/16; 433/17; 433/140

(58) Field of Classification Search
USPC .............. 128/848, 859–861, 201.26, 206.29, 128/200.24, 200.26, 207.14, 857; 433/93, 433/140, 21, 10, 11, 16, 17; 267/4
See application file for complete search history.

(56) References Cited

U.S. PATENT DOCUMENTS

| | | | |
|---|---|---|---|
| 587,358 A | 8/1897 | Anderson | |
| 746,869 A | 12/1903 | Moulton | |
| 774,446 A | 11/1904 | Moulton | |
| 1,389,436 A * | 8/1921 | Cameron | 600/219 |
| 1,674,336 A | 6/1928 | King | |
| 2,424,533 A | 7/1947 | Faires | |
| 2,614,325 A * | 10/1952 | Hartig | 433/138 |
| 2,651,300 A * | 9/1953 | Fehrman | 600/244 |
| 2,756,742 A | 7/1956 | Barton | 128/15 |
| 2,882,893 A | 4/1959 | Godfroy | 128/136 |
| 3,132,647 A | 5/1964 | Corniello | 128/136 |
| 3,857,181 A | 12/1974 | Rappaport | 32/36 |
| 4,041,937 A * | 8/1977 | Diaz | 600/240 |
| 4,071,026 A | 1/1978 | Bevins | 128/147 |
| 4,112,936 A | 9/1978 | Blachly | 128/136 |
| 4,169,473 A | 10/1979 | Samelson | 128/136 |
| 4,170,230 A | 10/1979 | Nelson | 128/139 |
| 4,200,089 A | 4/1980 | Inoue | 128/12 |
| 4,261,354 A | 4/1981 | Nelson | 128/203.23 |
| 4,262,666 A | 4/1981 | Nelson | 128/203.23 |
| 4,275,725 A | 6/1981 | Nelson | 128/207.14 |

(Continued)

Primary Examiner — Patricia Bianco
Assistant Examiner — Brandon L Jackson

(57) ABSTRACT

The cheek pocket anchor, formed of a resilient filament, fits within a user's cheek pouch. The anchor dynamically spans a user's inter-occlusal space and lip opening as a user's jaws open and close. The anchor can be formed of inter-connected, adjustable loops to enable user adjustment of its whole span. It can stabilize a work piece, such as an airway, in a user's mouth. The cheek path airway fits a path between a user's lips and through the user's cheek pouch and rear-jaw gap, avoiding the user's bite. It provides supplemental air to a user's rear-mouth cavity independently of a user's nasal airways while a user's lips remain closed. It can be used in combination with mandibular jaw-control and tongue-control devices whereby the combination mitigates breathing restrictions in a user's nasal and throat airways. It can be manufactured in-line and folded by a user to fit the user's cheek pathway.

5 Claims, 11 Drawing Sheets

U.S. PATENT DOCUMENTS

| | | | | |
|---|---|---|---|---|
| 4,289,127 A | 9/1981 | Nelson | | 128/207.14 |
| 4,304,227 A | 12/1981 | Samelson | | 128/136 |
| 4,553,549 A | 11/1985 | Pope et al. | | 128/421 |
| 4,669,459 A | 6/1987 | Spiewak et al. | | 128/136 |
| 4,715,368 A | 12/1987 | George | | 128/136 |
| 4,889,327 A | * 12/1989 | Seyler | | 267/168 |
| 4,992,046 A | 2/1991 | Sharp | | 433/93 |
| 5,003,994 A | 4/1991 | Cook | | 128/848 |
| 5,046,512 A | 9/1991 | Murchie | | 128/848 |
| 5,092,346 A | 3/1992 | Hays et al. | | 128/848 |
| 5,117,816 A | 6/1992 | Shapiro et al. | | 128/200.24 |
| 5,199,872 A | * 4/1993 | Leal | | 433/136 |
| 5,313,960 A | 5/1994 | Tomasi | | 128/848 |
| 5,427,117 A | 6/1995 | Thornton | | 128/848 |
| 5,465,734 A | 11/1995 | Alvarez et al. | | 128/848 |
| 5,507,284 A | 4/1996 | Daneshvar | | 128/207.14 |
| 5,566,683 A | 10/1996 | Thornton | | 128/848 |
| 5,642,738 A | 7/1997 | Lilly, Jr. | | 128/848 |
| 5,649,540 A | 7/1997 | Alvarez et al. | | 128/848 |
| 5,682,903 A | 11/1997 | Meade | | 128/848 |
| 5,740,791 A | 4/1998 | Aves | | 128/200.26 |
| 5,755,219 A | 5/1998 | Thornton | | 128/201.18 |
| 5,813,857 A | 9/1998 | Hertz | | 433/93 |
| 5,829,441 A | 11/1998 | Kidd et al. | | 128/848 |
| 5,868,138 A | 2/1999 | Halstrom | | 128/848 |
| 406,647 A | 3/1999 | Wagner | | |
| D406,647 S | 3/1999 | Wagner | | D24/181 |
| 5,894,840 A | 4/1999 | King | | 128/200.26 |
| 5,915,385 A | 6/1999 | Hakimi | | 128/848 |
| 5,921,240 A | 7/1999 | Gall | | 128/848 |
| 5,927,276 A | * 7/1999 | Rodriguez | | 128/207.17 |
| 5,941,246 A | 8/1999 | Roopchand | | 128/207.14 |
| 5,954,048 A | 9/1999 | Thornton | | 128/201.18 |
| 5,957,133 A | 9/1999 | Hart | | 128/207.14 |
| 6,244,865 B1 | 6/2001 | Nelson et al. | | 433/140 |
| 6,247,926 B1 | 6/2001 | Thornton | | 433/48 |
| 6,263,877 B1 | 7/2001 | Gall | | 128/848 |
| 6,273,713 B1 | * 8/2001 | Liou | | 433/19 |
| 6,305,376 B1 | 10/2001 | Thornton | | 128/848 |
| 6,408,851 B1 | 6/2002 | Karell | | 128/848 |
| 6,428,316 B1 | * 8/2002 | Rodriquez | | 433/92 |
| 6,450,167 B1 | 9/2002 | David et al. | | 128/848 |
| 6,494,209 B2 | 12/2002 | Kulick | | 128/848 |
| 6,516,805 B1 | 2/2003 | Thornton | | 128/848 |
| 6,533,761 B2 | 3/2003 | Bertoch et al. | | 604/174 |
| 6,561,192 B2 | 5/2003 | Palmer | | 128/207.17 |
| 6,702,739 B2 | * 3/2004 | Levisman | | 600/217 |
| 2002/0000117 A1 | 1/2002 | McCoy et al. | | |
| 2002/0117178 A1 | 8/2002 | Dort | | 128/860 |
| 2005/0252514 A1 | * 11/2005 | Taljaard | | 128/207.14 |

* cited by examiner

CHEEK PATH AIRWAY AND CHEEK POUCH ANCHOR

CROSS REFERENCE TO RELATED APPLICATIONS

There are no related applications.

STATEMENT REGARDING FEDERALLY SPONSORED RESEARCH OR DEVELOPMENT

No federally-sponsored research and development is involved.

THE NAMES OF THE PARTIES TO A JOINT RESEARCH AGREEMENT

Not applicable.

BACKGROUND OF THE INVENTION

1. Field of the Invention

The field of the invention is oral conduits for fluids, including oral airways.

2. Background Art

Nasal Breathing Restrictions.

Some persons at times breathe nasally during sleep, with the lips and jaws closed, thereby eliminating the mouth as an effective airway. Closed-mouth, nasal breathing through restricted nasal air ways reduces ventilation volume and can impair breathing and sleep. Restrictions in the nasal airway path may significantly contribute to breathing insufficiency during sleep in some persons who breathe nasally with lips closed. Scientific and medical experts have reported (or hypothesized) a variety of contributing and causal factors other than nasal airway restriction for hypopnea and apnea, such as sagging of the base of the tongue, and possibly the lower jaw, towards the throat, resulting in restriction or blockage of the throat air way. Nasal restrictions may contribute to snoring and to sleep apnea.

Jaw and Tongue Control Devices.

A variety of devices has been developed and patented by others to mechanically control a user's jaw and tongue positions to minimize sagging of tongue and mandible towards the user's throat airway. Some include oral airways. Others are designed to function during closed-mouth, nasal breathing.

It is an objective of the instant cheek airway invention that it be capable of placement and use in combination with a wide variety of exiting jaw- and tongue-control devices, though perhaps with some modification of such devices.

Tongue-Control Devices.

A non-exhaustive list of examples of tongue-control devices that incorporate airways or employ positive or negative air pressure is:

Alvarez, et al., U.S. Pat. No. 5,465,734 (1995); Hart, U.S. Pat. No. 5,957,133 (1999); Karell, U.S. Pat. No. 6,408,851 B1, discloses a tongue-fastening device having airway 40 and two or more internal airway openings 42 which, as depicted in Karell's FIGS. 3 and 5, pass between the teeth. Kulick, Pub. No.: US 2002/0139375 A1 holds the tongue forward by suction, uses bite blocks 2 to prevent biting the tongue and support air passages 4 into the oral cavity. Nelson, U.S. Pat. No. 6,244,865 B1, discloses a tongue positioning device which includes a hollow passageway 20 in the mouthpiece for flow of breathing gasses into the mouth.

Mouthpieces and Lip-Passing Tubes.

There exists an enormous variety of mouthpieces and other devices for delivery of gasses past the user's lips into the user's mouth. Examples include snorkels and SCUBA (Self-Contained Underwater Breathing Apparatus) mouthpieces, as well as tubes, cannulae and ventilators used in medicine, surgery, anaesthesia, orthodontics, and sports. There also are numerous devices designed to ameliorate some aspect of nasal congestion, snoring, hypopnea and apnea. Some airway devices simply provide conduits to external air at ambient pressure, whereas others are designed to deliver gasses at modified pressures. Examples of the latter are CPAP (Continuous Positive Airway Pressure) and BiPAP (Bi-level Positive Airway Pressure) machines.

Many existing oral airways pass between a user's maxillary and mandibular teeth, requiring bite blocks or other devices to prevent crushing of the airway between the teeth and thus restricting the user's jaw motion.

Devices Using Portions of the Cheek Pathway.

Nelson, in a series of U.S. Pat. Nos. 4,170,230, (1979), 4,261,354 (1981), 4,262,666 (1981) and 4,289,127 (1981), discloses several different versions of hollow tubes which traverse portions of a user's cheek pathway. Nelson's devices are designed for stand-alone cheek-side positioning; that is, they are not anchored to teeth-engaging or palate-engaging dental devices. Nelson does not disclose any structure curving around a user's rear-tooth corner, or passing into or through a user's rear-jaw gap, or extending from the user's rear-jaw gap over the user's tongue into airspace in a user's rear-mouth cavity. Nelson describes and depicts his curved tube as open-ended, with at least one opening internal to the user's mouth, and having a length to insure that there will be an air flow opening approximate the molars at the rear of the user's mouth. See, for example, Nelson, U.S. Pat. No. 4,170,230, abstract; column 1:25-38; column 2:55-67; column 3:19-35; column 4: 5-14; claims 1 and 6; and FIGS. 1, 2, 3, 5 and 7. Nelson's disclosure states that the air flow opening(s) of Nelson's tube "pass the air from the tube to the rear of the mouth and upper trachea." Since Nelson does not disclose any tube structure dorsal of the user's molars, Nelson leaves a reader to guess the path which air traverses after exiting Nelson's tube "approximate the molars." Nelson, U.S. Pat. No. 4,170,230, column 1, lines 44-47; column 4, lines 5-13; and abstract.

Nelson's patents, and especially U.S. Pat. No. 4,289,127 (1981), also disclose various cheek-side stabilizing devices including fin-like, wire-like and rod devices. Nelson describes his cheek-side stabilizing devices as rigid or flexible or malleable, but does not describe them as resilient or spring-like.

Pope and Hawkins, U.S. Pat. No. 4,553,549, disclose a "pressure equalization conduit" attached to an orthopedic/orthodontic appliance for treating neuromuscular imbalance which is positioned "so that the tube extends along the outside surface of the teeth around the posterior of the teeth to the position which is in communication with the pharyngeal cavity." Pope, et al., U.S. Pat. No. 4,553,549, specification col. 3:10-20 and claim 13. (Pope's "posterior" presumably corresponds to dorsal.) In contrast with Nelson's cheek-side tubes, the pressure equalization conduit of Pope, et al., is not disclosed as a self-contained device designed to stand alone in a cheek pathway. Rather, the Pope conduit is positioned by wire holders that are embedded in the teeth- and palate-engaging elements of the Pope orthopedic/orthodontic device. Pope et al. U.S. Pat. No. 4,553,549, col. 5:60-68. At least one version of the Pope conduit is disclosed and is explicitly claimed as having "inside diameter of from about 2 to 3 mm." Pope, Specification, 3:30-40 and claim 16. However, Pope, et al. do not state limiting diameters.

BRIEF SUMMARY OF THE INVENTION

This application discloses a cheek path airway and a cheek pouch anchor. In a preferred version, they are combined with each other, but each also could be used alone or in combination with other prior art devices. Such other prior art devices include jaw control and tongue control devices.

Summary of Cheek Path Airway Invention. The cheek path airway is a hollow tube or channel configured, or adjustable, to act as a conduit for air or other fluids along a user's "cheek pathway." A user's "cheek pathway" is defined more precisely below.

The cheek path airway bypasses nasal airways and provides oral air flow supplemental to nasal flow, even though the user's lips, teeth and jaws are otherwise closed. Thus, the cheek path airway can provide supplemental air volumes to mitigate breathing impairment caused by restriction of a user's nasal airways without a user having to switch to open-mouth breathing.

The cheek path airway's curve from the cheek-side to the dorsal side of a user's rear-most teeth helps constrain rotational and translational motions of the airway tube in a user's mouth. When a user's jaws are opened the cheek path airway alone (without the cheek pocket anchor) remains somewhat vulnerable to rotating or sliding between the biting surfaces of a user's teeth. The airway can be built to mitigate such motions by using a relatively stiff (or stiffly flexible) curve through the user's rear-jaw gap, and by forming (or flexing) the tongue portion of the airway to conform relatively stiffly to the side and roof of the user's rear-mouth cavity, while more rigid portions of the airway extend along the inner wall of a user's cheek and between a user's lips.

The cheek path airway can be made flexible or moldable at strategic positions along its longitudinal axis so that the action of the user's tongue and jaws will press the airway into locations of lesser interference with movements of the user's tongue and rear-jaw gap, thus achieving better fit and stability.

External extensions of the cheek path airway, which curve about the outside corner of a user's mouth and traverse along the user's external cheek wall, can be employed to further constrain the airway in a cheek pathway. Stability can be further improved by an external extension which folds about a user's ear.

A dual cheek path airway, which traverses the two cheek pathways on either side of a user's mouth, can further increase stability as well as increasing air flow volume and providing redundant conduits.

More positive control over destabilizing motions of a cheek path airway can be achieved by combining the cheek path airway with a cheek pouch anchor.

Summary of Cheek Pouch Anchor Invention. The cheek pouch anchor is a spring element which is adapted to be placed within a user's "cheek pouch," an area which lies between the inner wall of a user's cheek and such user's gums and teeth as more precisely defined elsewhere in this disclosure. The cheek pouch anchor of the instant invention can expand and compress in a resilient or spring-like manner within a user's cheek pouch as a user opens and closes the user's jaws. A cheek pouch anchor can better maintain a cheek path airway's positioning while avoiding the more-mobile ventral portions of a user's tongue, avoiding the biting surfaces of the user's teeth, resisting expulsion from the user's mouth, and mitigating risks of choking and gagging.

The cheek pouch anchor invention is capable of receiving joinder to a work piece that is to be positioned at least partially within such user's cheek pouch. The cheek path airway is one type of work piece that can be joined to the cheek pouch anchor.

It is conceived that the cheek pouch anchor could be impregnated or coated with substances that are intended to be released over time within a user's mouth, or it could carry and position containers and other devices at least partially within a user's cheek pouch.

Summary of Combination of Cheek Path Airway and Cheek Pouch Anchor Inventions.

The combination of the cheek path airway and the cheek pouch anchor provides additional constraints upon rotations and translations of the cheek path airway, beyond the constraints built into the cheek path airway itself, which render the combination more suitable for use during sleep.

Summary of Combination of Cheek Path Airway With Existing Jaw- and Tongue-Control Devices. The cheek path airway can be used (with or without the cheek pouch anchor) in combination with a mandibular jaw control device that restricts sagging of a user's mandible toward such user's throat airway during sleep for the purpose of mitigating throat airway impairment and sleep apnea. It is conceived that the cheek path airway also could be used in combination with many other dental, jaw, and tongue control devices. The cheek path airway can functionally leverage itself against a dental device installed in a user's mouth so as to improve the airway's stability within the cheek pathway, but without substantial impairment of the function of such dental device, so that the combination functions cooperatively to mitigate a user's breathing problems.

Some Special Anatomical Definitions. The following definitions have been created for the purposes of this disclosure and the claims:

"User" means the creature using a device, generally a human, though devices in principle could be used by creatures other than humans.

"User's anterior-posterior axis" means head to foot for a human user, head to tail for other creatures. Sometimes also called a "vertical" axis when a human is viewed standing upright.

"User's dorsal-ventral axis" means back to front, that is, with a human user's face in front; such axis is approximately horizontal when an upright human user is viewed. Also sometimes referred to as front and rear.

"User's cheek pathway", sometimes abbreviated to "cheek pathway" or "cheek path", means the pathway, traversing in either direction, from (1) outside the user's mouth, (2) between such user's lips, (3) between such user's inner cheek wall and the cheek-adjacent side of such user's dental arches, gums and teeth, and (4) at least around the cheek-side rear tooth corner of such user's rear-most tooth or teeth from cheek side to dorsal side of such tooth. The cheek pathway can be further extended (5) from the user's cheek-side rear tooth corner through such user's rear-jaw gap, and yet further extended (6) from such user's rear-jaw gap over such user's tongue into the airspace in such user's rear-mouth cavity. The cheek pathway avoids the biting (occlusal) surfaces of a user's teeth.

"User's cheek pouch" lies between the inner wall of one of such user's two cheeks and the cheek-adjacent side of such user's dental arches, gums and teeth. A user's cheek pouch extends along such user's anterior-posterior ("vertical") body axis between the junctures of such user's mandibular and maxillary dental arches with such user's inner cheek wall. Such cheek pouch extends along such user's dorsal-ventral body axis approximately from a user's front teeth to the general area of such user's most-dorsal teeth and rear-jaw gap. The configuration of a user's cheek pouch dynamically alters as the user's jaws and lips open and close. A user has two cheek pouches located on opposing sides of a user's mouth.

"User's cheek-side position" means a location adjacent to a user's inner cheek wall, within the user's cheek pouch, in which a device can be placed.

"User's rear-jaw gap" or "rear-jaw space" means the space remaining open between such user's mandible (lower jaw) and maxilla (upper jaw) dorsally of such user's rear-most tooth or teeth when such user's jaws are closed. The size and shape of the rear-jaw gap will vary from person to person. It is sufficiently large in some persons to accommodate a cheek path airway. Sometimes the rear-jaw gap has been enlarged by extraction of at least one of the person's wisdom teeth. A user's rear-jaw gap also can be artificially enlarged by dental devices which partially block the user's bite and prevent complete closure of the user's jaws. A user generally will have two rear-jaw gaps, one on each side of the user's head.

"Air" as used herein includes any gasses or other fluids for inhalation and exhalation by humans or other creatures. "Air" could include natural environmental air at atmospheric or other pressure and partially or wholly modified gasses and fluids such as supplemental oxygen, mixtures of gasses, aerosols, and oxygenated fluids, whether or not at atmospheric pressure. It is conceived that the cheek path airway could conduct fluids other than "air", including without limitation, pharmaceutical and anesthetic gasses.

The Problems Addressed by the Invention

Nasal airway restriction causes a variety of adverse effects, ranging from the merely uncomfortable to life threatening. The mouth provides an alternate, natural breathing airway, but not when a person's lips are closed.

Many airway devices use a mouth pathway to bypass restricted nasal passages. All airways which use a mouth pathway must be stabilized in the mouth to mitigate risks of gagging and choking and to prevent ejection from the mouth or displacement within the mouth. These problems of stable positioning of a mouth airway are particularly critical while a user is asleep or otherwise is unconscious. The instant invention mitigates stability problems of stand-alone cheek-side airways. It also mitigates blockage of air flow openings.

All mouth airway devices must use materials which are essentially non-toxic to the user, and the instant invention is intended to do so.

Most mouth airway devices are "central mouth" airways which pass between the biting surfaces of a user's teeth. Such devices thus must use some form of bite block to prevent closing of the user's jaws and teeth from crushing the airway. The instant invention can function with or without a bite block in place.

Many central airway devices are anchored by dental devices that engage the user's teeth or dental arches or palate. Such devices create a potential for undesired orthodontic effects from the airway anchoring and from bite blocking. One orthopedic/orthodontic device is designed to be installed within a user's maxillary dental arch to actively modify a user's mouth anatomy, and it also includes a "pressure equalization conduit" which is positioned in a cheek pathway. Pope et al., U.S. Pat. No. 4,553,549. Use of dental anchoring adds complexity and expense to a cheek path airway device and tends to encumber a user's jaw and tongue movements. It is desirable to have a mouth airway which by-passes, and is not anchored to, a user's teeth or palate.

The airway of the instant invention bypasses, and is not anchored to, a user's teeth or palate. It avoids the more-mobile ventral portions of a user's tongue and enables the more dorsal portions of a user's tongue to press the airway into positions of lesser interference with the tongue's movements in the user's rear-mouth cavity.

It can be desirable to preserve some nasal breathing even when nasal passages are restricted. Nasal passages provide a variety of desirable natural breathing features such as filtering, warming and moisturizing the air, and avoidance of high volumes of air flow past teeth, gums and tongue. It also is desirable to have a mouth airway which allows the user's lips to nearly seal about it so as to route air through the airway and avoid open-mouth breathing. Full open mouth breathing causes "dry mouth" discomfort. Because the open mouth provides such a large pathway, open mouth breathing tends to nearly pre-empt nasal breathing, especially if the nasal passages are restricted. Some mouth airway devices aim to function as a complete alternative to nasal breathing while avoiding full open-mouth breathing. For example, Nelson's tube is designed so that "the flow of air therefrom will be approximate to that flow of air as could be expected from normal nasal breathing," (Nelson, U.S. Pat. No. 4,170,230, Abstract).

The instant invention is designed to supplement, but not necessarily to replace, nasal breathing. It thus can help preserve some nasal breathing. It can function during periods of restricted nasal breathing before a user has switched from closed-mouth nasal breathing to open-mouth breathing.

Problems with Cheek-side Positioning of Airways.

Some mouth airways, herein called "cheek-side" airways, are designed for placement between the inner wall of a user's cheek and a user's cheek-adjacent gums and teeth in order to avoid the biting surfaces of a user's teeth and the user's tongue. This "cheek-side" location is only a portion of what is defined in this disclosure as a full "cheek pathway". The Nelson airways, U.S. Pat. Nos. 4,170,230, (1979), 4,261,354 (1981), 4,262,666 (1981) and 4,289,127 (1981), for example, are designed to lie in a cheek-side position.

Cheek-side Air-flow Openings Subject to Blockage and Saliva Drainage. Air-flow openings placed in a cheek-side position are subject to blockage by the user's cheek, gum and tooth tissues and by mouth liquids. They also tend to drain liquids into the airway tube and out of the user's mouth. As a result, there is a relatively small margin for error in cheek-side positioning of air flow openings.

A user's inner cheek wall naturally, resiliently drapes over the cheek-adjacent side of a user's dental arches, teeth and gums. It will tend to drape over an airway device in a cheek-side position, urging the airway against the user's dental arches, gums and teeth. This draping effect can cause blockage of cheek-side air flow openings by the user's tissues, but the draping effect also provides forces that can be utilized to stabilize cheek-side devices.

The instant invention mitigates blockage of air flow openings by curving the cheek path airway around the user's rear-tooth corner from cheek side to dorsal side. This curve either exposes the airway's internal open tip to the user's rear-jaw gap, or, preferably, enables projection of the airway's internal open tip through the user's rear-jaw gap and over the user's tongue within the airspace in the user's rear-mouth cavity. The larger airspace volume within a user's rear-mouth cavity provides a larger margin of error in placement of air flow openings than does a cheek-side positioning of air flow openings adjacent to a user's teeth and gums. This positioning also tends to mitigate exposure of the tube opening to saliva and other mouth liquids.

Slippage and Rotation Problems of Cheek-side Airways.

Cheek-side airways have numerous modes of potentially undesirable motion, including the three axes of translational motions (anterior-posterior, dorsal-ventral, and side-to-side or "lateral"), as well as the three modes of rotational motion (roll, pitch and yaw).

Undesirable motions of a cheek-side airway include: slippage of the device between the biting surfaces of a user's teeth; interference with the user's tongue motions; slippage into gagging or choking positions; dorsal-ventral slippage of the device between the user's lips, and expulsion from the user's mouth.

In Nelson's tubes, for example, undesirable rotation of the tube caused blockage of air openings by the user's mouth tissues. Nelson's tubes also were subject to dorsal-ventral slippage. Nelson, U.S. Pat. No. 4,289,127, col. 1:35-45. Nelson developed cheek-side stabilizing devices to mitigate undesirable rotational motions (see particularly U.S. Pat. No. 4,289,127), as well as to prevent dorsal-ventral slippage and impairment of the user's lip seal (see U.S. Pat. Nos. 4,170,230, 4,261,354, 4,262,666, 4,275,725, and 4,289,127).

Fixed-span cheek-side stabilizing devices, such as the fin-like, wire-like and rod devices of Nelson, have a potentially disabling instability problem. Such fixed-span devices cannot dynamically adjust to maintain a span across the gap (inter occlusal space) created between a user's maxillary and mandibular teeth as the user's jaws open. However, a user's jaws sometimes can open beyond that fixed-span height, allowing the fixed-span device to rotate or slip between the biting (occlusal) surfaces of the user's teeth.

Suppose, by way of hypothetical illustrative example, that the heights of a user's mandibular and maxillary dental arches are 1.75 cm each (measured from their respective junctures with the user's inner cheek wall to the biting surfaces of their respective teeth). The vertical height of such user's cheek pocket, when the user's jaws are closed, is the sum of the heights of the user's dental arches, that is, 3.5 cm. The height of the user's cheek pocket with jaws closed establishes the maximum vertical span of a fixed-span cheek-side stabilizing device because a greater fixed span would block full closure of the user's jaws. Whenever the user is capable of opening an inter occlusal space which exceeds the 1.75 cm height of one of the user's dental arches then the potential will exist for a fixed-span cheek-side stabilizing device to rotate or translate between the biting surfaces of such user's teeth. Suppose the user's jaws open an inter occlusal space of 2 cm. Then the sum of that 2 cm inter occlusal space and the 1.75 cm height of one dental arch will total 3.75 cm, which exceeds the 3.5 cm maximum fixed span of a cheek-side stabilizing device that would permit that user's jaws to fully close, thereby potentially permitting a fixed-span stabilizing device to slip or rotate into that 2.0 cm inter occlusal space. Such an inter occlusal space might occur, for example, during a yawn or a cough. Of course, the hypothetical dimensions used above would vary from user to user, but the principle should apply to many potential users.

The instant invention's solution to the instability problem of fixed-span cheek-side positioning devices is to use a spring which resiliently expands and compresses within the user's cheek pouch as the user's jaws open and close. The expansion of the resilient cheek pouch anchor of the instant invention when a user's jaws open can usefully increase the stability of a cheek-side airway over that of a fixed-span cheek-side stabilizing device even if the resilient device is unable to expand the full vertical height of a user's maximum jaw opening. This is because most jaw openings are less than the maximum potential jaw opening.

Lip-Sealing Problems.

Cheek-side airway tubes pass between a user's lips and thus can break the seal of the user's lips, permitting air passage around rather than through the tube. This lip sealing problem tends to increase with increasing tube diameter and certain variant shapes. There are many prior art lip-sealing devices.

Mouth-Corner Flanges. Nelson's patents, and especially U.S. Pat. Nos. 4,170,230 and 4,275,725, disclose modifications of Nelson's tube by flanges which engage the corner of a user's mouth and the user's lips for purposes of stabilizing the tube and sealing the user's lips.

Lip-conforming Tube Shapes. It is known that use of a tube lip portion which has an oval or somewhat flattened radial cross-section can improve sealing of the user's lips. That known solution can be employed in the instant invention.

Objectives and Features of the Invention

Objectives of this invention include the following:

An objective of this invention is to provide a relatively stable, supplemental ventilation pathway through a user's closed lips to the rear of the user's oral cavity which will remain open during closed-mouth, nasal breathing.

An objective of this invention is to provide supplemental air to a user's throat when a user's lips otherwise remain closed for the purpose of mitigating adverse effects of restricted nasal airways without requiring that the user switch from closed-mouth nasal breathing to open-mouth breathing.

An objective of this invention is to provide an airway passing from external air through a user's otherwise-closed lips to the rear of the user's oral cavity, while by-passing the user's jaws, tooth biting surfaces, and much of the user's tongue, including the more mobile forward portions of the user's tongue. In particular, it is an objective of this invention to provide an airway which can stabilize itself within in a user's cheek pathway without anchoring to a user's teeth, thus permitting opening and closing of the user's jaws without disruption of the airway's cheek pathway positioning.

An objective of this invention is that it not physically prevent or restrict a user from switching from closed-mouth nasal breathing to open-mouth breathing.

It is an objective of this invention that it provide one or more passive air ways past closed lips which will remain relatively stable in a sleeping person, notwithstanding lip, jaw and tongue motions.

It is an objective of this invention that it have a shape and be positioned so as to minimize gagging or choking risk to a user of this invention, particularly while sleeping.

It is an objective of this invention that it remain relatively resistant to blockage of air flow openings by the cheek wall, gums, teeth, tongue or other tissue in a user's mouth.

It is an objective of this invention that it be capable of being placed so that it minimizes transmission of saliva or other mouth liquids through the airway past a user's lips.

It is an objective of this invention that it mitigate the "dry mouth" distress which many persons experience with open-mouth breathing by supplementing and preserving closed-mouth nasal breathing. It is an objective of this invention to deliver supplemental air directly to the rear of a user's oral cavity with a user's lips otherwise closed, minimizing air currents in more ventral portions of a user's mouth.

It is an objective of this invention that lay persons be capable of inserting, adjusting, using, and removing it by themselves.

It is an objective of this invention that it be adjustable to fit a particular user's comfort.

It is an objective of this invention that it be sanitizable by the same processes used for ordinary household eating utensils, such as dishwashing machines, or by the processes used for artificial dentures.

It is an objective of this invention to provide a supplemental air way to the rear of a user's mouth cavity which can function in combination with devices designed to control a user's tongue, tooth and/or jaw position, so the combination can cooperatively mitigate impaired breathing due to restriction of the user's nasal and throat airways. It also is an objective that the airway be compatible, and function in combination, with an anti-bruxing dental device. One useful effect, where such jaw-control or anti-bruxing devices block full closing of a user's jaws, is that such devices can increase the cross-sectional area of a user's rear-jaw gaps which thereby more easily accommodate a larger diameter cheek path airway.

Jaw-control and Tongue-Control Devices.

Examples of existing intra-oral, jaw-control and tongue-control devices with which it is conceived the invention might be used in combination (perhaps requiring some modification) are:

Fenton, U.S. Pat. No. 5,499,633; Halstrom, U.S. Pat. No. 5,868,138; Strong, U.S. Pat. No. 6,418,933; Thornton, U.S. Pat. No. 6,325,064 B1; Meade, U.S. Pat. No. 6,055,986; Belfer, U.S. Pat. No. 6,092,523; Frantz, U.S. Pat. No. 6,109,625; Bergersen, U.S. Pat. No. 6,129,084; Thornton, U.S. Pat. No. 6,155,262; David, U.S. Pat. No. 6,450,167 B1; Tielmans, U.S. Pub. No. 2001, 0027793 A1 and U.S. Pat. No. 6,408,852 B2; Gaskell, U.S. Pub. No. 2002/0000230 A1; and Dort, Pub. No. US 2002/0117178 A1 (August 2002). See also Thornton, U.S. Pat. No. 6,209,542 (nasal mask combined with dental device). Wagner, U.S. Pat. No. 5,566,684 (1996) discloses a mouthguard which a user can self-fit to the user's maxillary dentition to mitigate nocturnal teeth grinding. An embodiment of Wagner's device, with instructions for self-fitting by users, is marketed under the trade name "The Doctor's Night Guard", by Dental Concepts, Paramus, N.J., USA. There are advantages where a cheek-path airway is physically separated from the jaw-control and tongue-control devices, but designed to be used in a user's mouth in combination with such devices. The cheek-path airway then can be inserted or removed separately from the jaw- or tongue-control device, enabling separate handling of the cheek-path airway and such devices, such as separate fitting, adjustment, cleaning, and replacement. Moreover, it is conceived that existing jaw- and tongue-control devices which do include built-in airways could be simplified, and thus more readily constructed, if such built-in airways are deleted and their function replaced by a physically separate cheek-path airway adapted for combination use with such modified devices.

TABLE OF DRAWING ELEMENTS

Cheek Path Airway Elements

Figure 1:
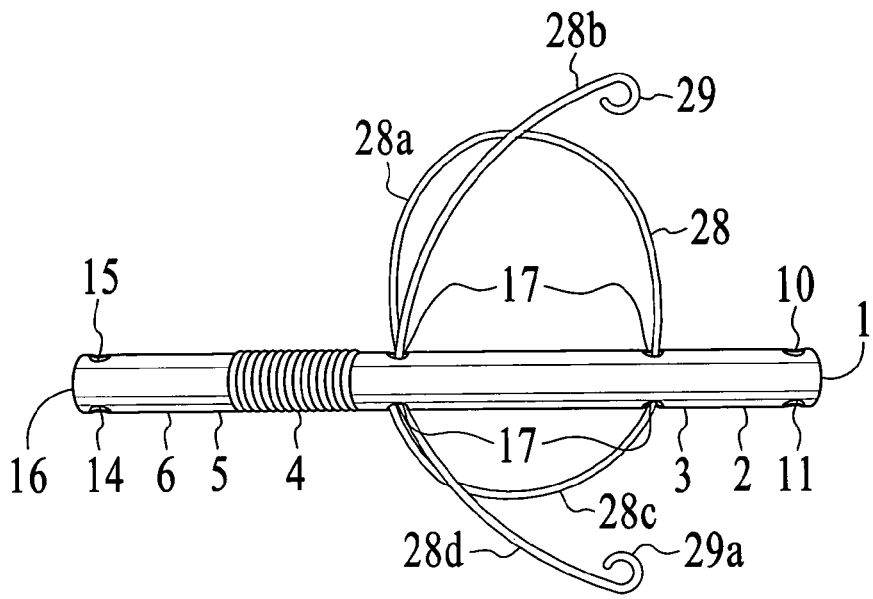
FIG. 1 is an elevation view of a cheek path airway combined with a cheek pouch anchor.

1 external open tip of hollow tube, to be positioned external to user's lips

1a external open tip on second end of hollow tube in dual-cheek version of airway

2 lip portion of hollow tube, for traversing between user's lips

2a second lip portion of hollow tube in dual-cheek version of airway

3 cheek-side portion of hollow tube, to be positioned between inner side of user's cheek and cheek-adjacent (buccal) side of user's teeth and gums

3a second cheek-side portion of hollow tube in dual-cheek version of airway

4 rear-tooth corner portion of hollow tube; curved, or flexible, transition from cheek-side portion to jaw-gap portion of hollow tube, adjacent to rear-most tooth.

4a rear-tooth corner portion, curved, or flexible, transitioning from cheek portion to jaw-gap portion of hollow tube, adjacent to rear-most tooth in dual cheek version of airway.

5 rear-jaw gap portion of hollow tube (may be straight, or curved, or flexible)

5a Second rear-jaw gap portion of hollow tube in dual cheek version of airway.

6 Tongue portion of hollow tube, to extend from rear-jaw gap over user's tongue into user's rear mouth cavity (may be straight, or curved, or flexible).
6a Second tongue portion of hollow tube in dual cheek version of airway.
7 Rear-mouth cavity-spanning portion of hollow tube in dual cheek version of airway; joins first and second cheek-side portions 8 and 9 of dual cheek version.
8 First cheek-side portion of hollow tube in dual cheek version of airway, to traverse user's first cheek pathway on first side of user's mouth
9 Second cheek-side portion of hollow tube in dual cheek version of airway, to traverse user's second cheek pathway on second side of user's mouth.
10 air flow opening in first position in wall of external end of hollow tube
10a air flow opening in first position in wall of second external end of hollow tube in dual cheek version
11 air flow opening in second position in wall of external end of hollow tube
11a air flow opening in second position in tube wall of second external end of hollow tube in dual cheek version.
12 air flow opening in first position in tube wall of tongue portion of hollow tube (tube portion 6)
12a air flow opening in first position in tube wall of second tongue portion of hollow tube (tube portion 6a) in dual cheek version
13 Air flow opening in second position in tube wall of tongue portion of hollow tube.
13a Air flow opening in second position in tube wall of second tongue portion of hollow tube in dual cheek version.
14 Air flow opening in third position in tube wall of tongue portion near the center of the rear-mouth cavity in single cheek version of airway; alternately, located in hollow tube portion 7 in dual cheek version of airway.
15 Air flow opening in wall of hollow tube, in fourth position in tongue portion of hollow tube near the center of the rear-mouth cavity in single cheek version of airway; alternately, located in hollow tube portion 7 in dual cheek version of airway.
16 internal open end of hollow tube, located on tongue portion of hollow tube in single cheek version of airway, to be projected within airspace in user's rear-mouth cavity.
16a internal open end of second hollow tube, located on second tongue portion of second hollow tube in user's second cheek pathway, when two single cheek versions used in opposite cheeks.
17 lacing holes in cheek-side portion of hollow tube, adapted to receive flexible, resilient filament 28 of cheek positioning device.
18 reserved
19 reserved
Airway Retainer Elements
20 a first type of retainer on external end of hollow tube
21 reserved
22 a second type of retainer, mouth-corner portion of hollow tube, to curve from lip portion 2 of tube about corner of user's mouth to outside wall of user's cheek
23 External cheek-side extension of hollow tube.
24 Flexible (or curved) portion of external cheek-side extension of tube
25 Flexible (or curved) ear piece of external extension of tube
26 Finger grip portion of ear piece.
27 Tape site on external cheek-side extension of hollow tube, for taping tube to user's face.
Cheek Pouch Anchor Elements
28 Flexible, resilient filament
28a First (upper) loop in laced filament
28b second (upper) loop in laced filament
28c third (lower) loop in laced filament
28d fourth (lower) loop in laced filament
29 First curled (or crimped) end of filament
29a Second curled (or crimped) end of filament
User's Body Parts
30 user's upper lip
31 user's lower lip
32 inner wall of user's first cheek
32a inner wall of user's second cheek
33 user's upper (maxillary) rear-most (dorsal) tooth on first side of user's mouth
33a user's upper (maxillary) rear-most (dorsal) tooth on second side of user's mouth
34 lingual (tongue) side of user's rear-most upper (maxillary) tooth on first side of user's mouth
34a lingual (tongue) side of user's rear-most upper (maxillary) tooth on second side of user's mouth
35 buccal (cheek-adjacent) side of user's rear-most upper (maxillary) tooth on first side of user's mouth
35a buccal (cheek-adjacent) side of user's rear-most upper (maxillary) tooth on second side of user's mouth
36 user's upper jaw (maxilla) on first side of user's mouth
36a user's upper jaw (maxilla) on second side of user's mouth
37 user's lower jaw (mandible) on first side of user's mouth
38 user's rear-most (dorsal) lower (mandibular) tooth on first side of user's mouth.
39 user's tongue
40 roof of user's rear-mouth (oral) cavity
41 airspace in user's rear-mouth (oral) cavity
42 user's rear-jaw gap on first side of user's mouth
42a user's rear-jaw gap on second side of user's mouth
43 Occlusal (biting) surface of user's tooth.
44 User's uvula (depending from user's soft palate)
45 First corner of user's mouth (at juncture of upper and lower lips).
45a Second corner of user's mouth.
46 External wall of user's first cheek
47 User's first ear
48 Lower side of user's first ear
49 Upper side of user's first ear
50 Dotted approximate outline of user's cheek pouch (showed with user's cheek removed)
Dental Device Elements
51 upper (maxillary) portion of dental device (showed upside down in some drawings)
52 lower (mandibular) portion of dental device (showed upside down in some drawings)
53 female (or sleeve) portion of adjustable strut of dental device
54 male (or arm) portion of adjustable strut of dental device
55 pivot bolt for mounting adjustable strut in maxillary portion of dental device
56 pivot bolt for mounting adjustable strut in mandibular portion of dental device
57 collar of male (arm) portion of adjustable strut of dental device
58 collar of female (sleeve) portion of adjustable strut of dental device
59 wire reinforcing frame embedded in lower (mandibular) portion of dental device.

60 wire reinforcing frame embedded in upper (maxillary) portion of dental device.
61 series of teeth-engaging balls mounted on wire reinforcing frame 33 and projecting out of body of mandibular portion of dental device
62 channel fitted to user's mandibular teeth
63 channel fitted to user's maxillary teeth
64 dental device, with channel fitted to user's teeth

DETAILED DESCRIPTION OF THE INVENTION

FIG. 1 shows a cheek path airway combined with a cheek pouch anchor. The cheek path airway is formed of a hollow tube (showed as manufactured in-line, with approximately zero curvature along its longitudinal axis), having external open tip 1, lip portion 2, cheek-side portion 3, flexible rear-tooth corner portion 4, rear-jaw gap portion 5, tongue portion 6, air flow openings 10 and 11 in the tube wall placed adjacent to external open tip 1, and air flow openings 14 and 15 in the tube wall placed adjacent to internal open tip 16, with lacing holes 17 through the walls of the cheek-side portion 3 of the hollow tube. FIG. 1 also shows flexible, resilient filament 28, slidably laced through lacing holes 17 of the hollow tube, to form upper first loop 28a, upper second loop 28b bearing upper curled loop end 29, lower third loop 28c, and lower fourth loop 28d bearing lower curled loop end 29a. Loops 28a, 28b, 28c and 28d combine to form the whole loop span formed by the flexible, resilient filament 28. By tugging on curled loop ends 29 and 29a a user can lengthen loops 28b and 28d and shorten loops 28a and 28c; conversely, by tugging on loops 28a and 28c a user can lengthen those loops while shortening loops 28b and 28d, thus enabling a user to adjust the whole loop span of filament 28 for better fit.

Figure 2:
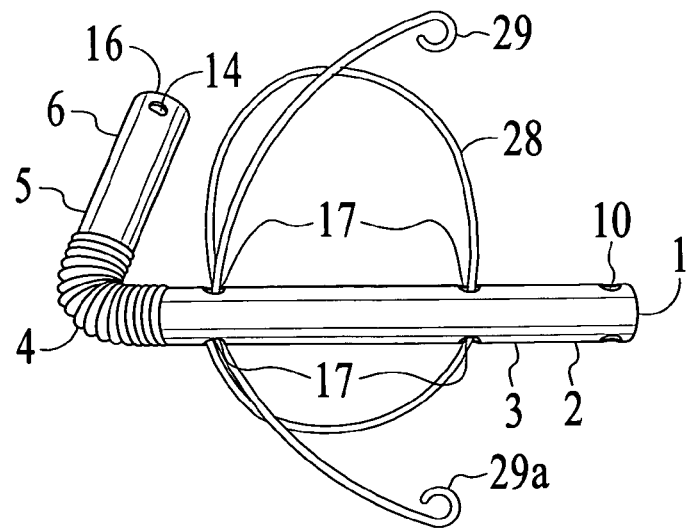
FIG. 2 is an elevation view of the same cheek path airway combined with a cheek pouch anchor, as is FIG. 1, but folded.

FIG. 2 shows the same cheek path airway combined with a cheek pouch anchor as in FIG. 1, but with the flexible rear tooth-corner portion 4 folded for positioning in a user's cheek pathway.

Figure 3A:
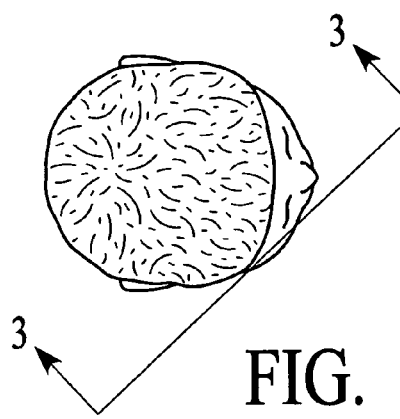
FIG. 3 is an elevation view of the side of a user's face showing a section view of the user's mouth, along Section 3-3 of FIG. 3A, with the user's cheek removed, showing placement of a cheek path airway combined with a cheek pouch anchor.
Figure 3:
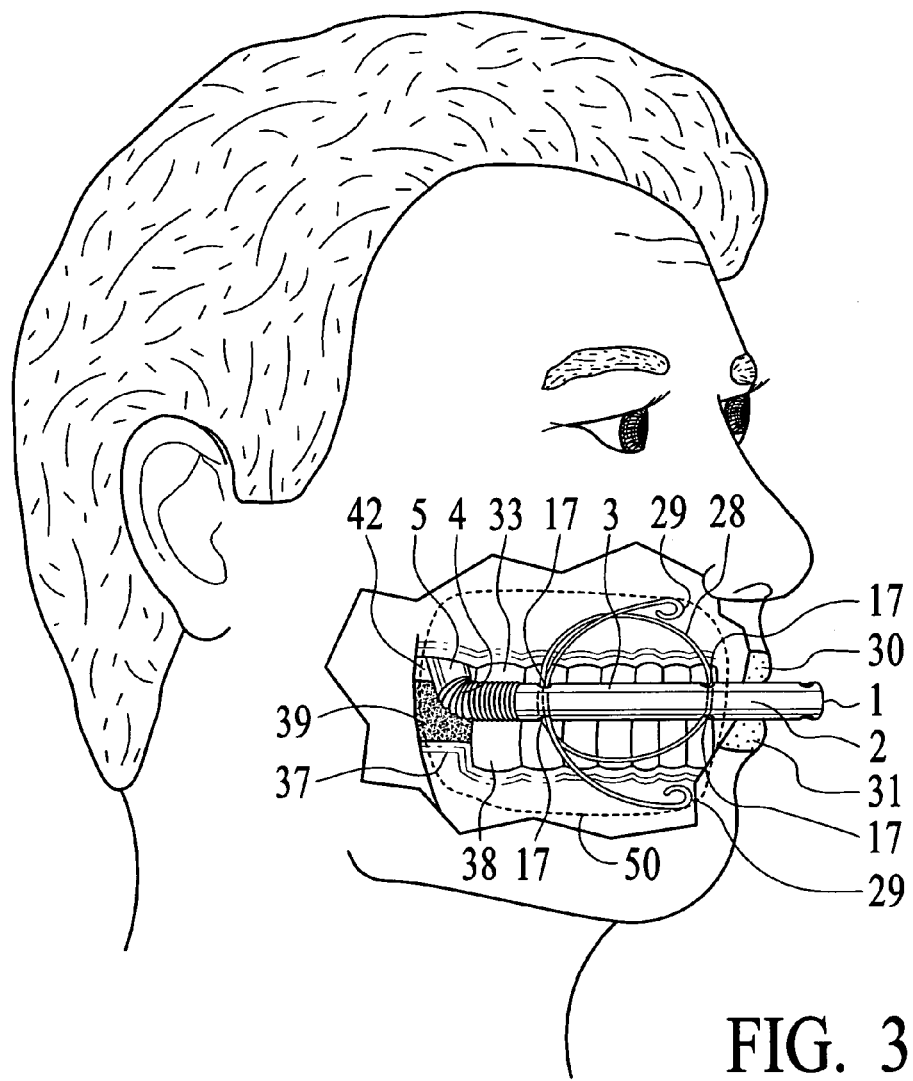

FIG. 3 depicts a cheek path airway combined with a cheek pouch anchor and placed in a user's cheek pathway and cheek pouch. FIG. 3 shows the hollow tube airway with external open end 1 in a position outside the user's lips, and lip portion 2 passing between the user's upper lip 30 and lower lip 31. FIG. 3 shows cheek-side portion 3 of the hollow tube lying adjacent to the buccal side of the user's teeth, with rear-tooth corner portion 4 of the hollow tube flexed about the user's rear-most (dorsal) upper tooth 33 and lower tooth 38. It shows airway rear-jaw gap portion 5 passing through user's jaw gap 42, adjacent to user's tongue 39. It shows flexible, resilient filament 28 laced through lacing holes 17 in cheek-side portion 3 of the hollow tube, and placed within the user's cheek pouch which is approximately outlined by the dotted line 50.

Figure 4A:
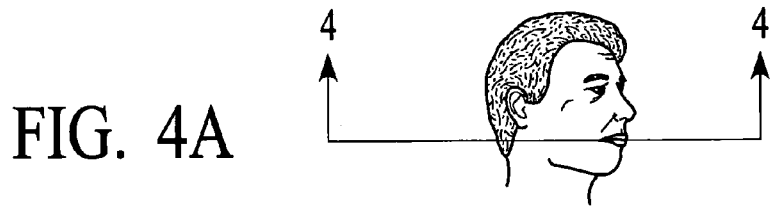
FIG. 4 is a section view, along section 4-4 of FIG. 4A, looking upward at the user's maxillary teeth and jaw with cheek path airways in place.
Figure 4:
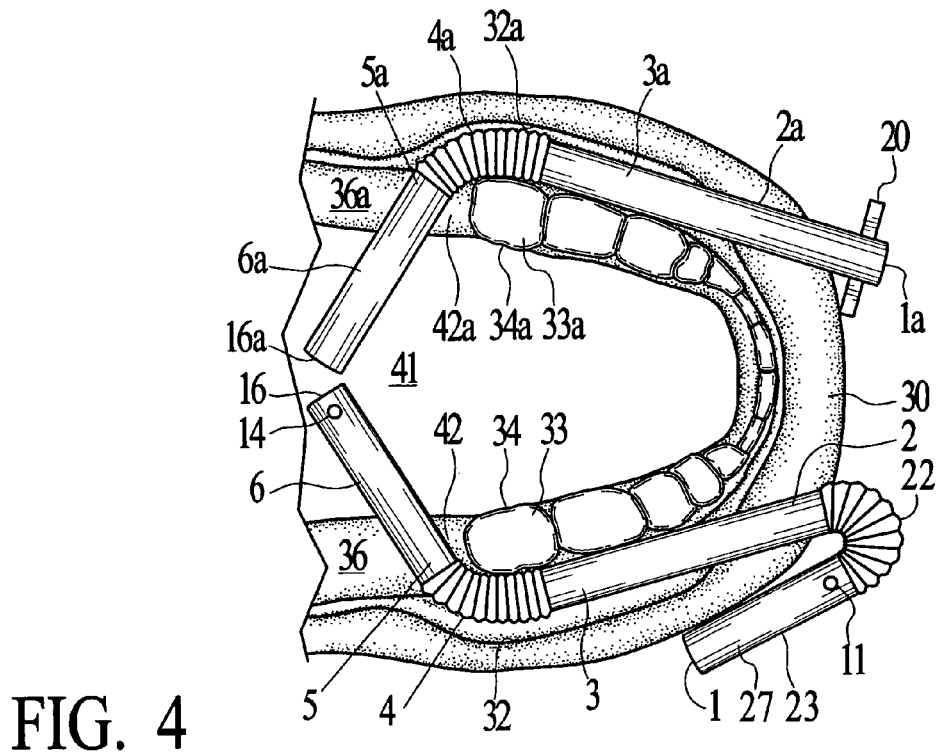

FIG. 4 depicts a section view, along section 4-4 of FIG. 4A, looking upward at a user's upper (maxillary) jaw and teeth. It shows two variants of the single-cheek version of the airway placed in the user's two cheek pathways on opposing sides of a user's mouth. In the user's first cheek pathway, in the lower part of the drawing, the hollow tube has external open end 1, with added mouth-corner portion 22 flexed to curve about the corner of the user's mouth to act as a retainer element, external cheek-side portion 23 bearing a tape site 27 for taping the tube to a user's cheek, and air flow opening 11. Lip portion 2 of the hollow tube passes the user's upper lip 30, cheek-side portion 3 passes between the user's inner cheek wall 32 and the buccal side of the user's teeth and gums, with rear-tooth corner portion 4 of the hollow tube flexed about the user's rear-most (dorsal), upper (maxillary) tooth 33, which tooth has a lingual side 34. Rear-jaw gap portion 5 of the hollow tube passes user's upper jaw (maxilla) 36 through the user's rear-jaw gap 42. Tongue section 6 of the hollow tube projects internal open end 16 of the hollow tube into the airspace 41 in the user's rear-mouth cavity. Adjacent to internal open end 16 is air flow opening 14 in the wall of the hollow tube. The upper portion of FIG. 4 shows the user's second cheek pathway with a second airway in place. The second airway is modified with retainer 20 placed adjacent to the external open tip 1a, positioned outside of user's upper lip 30.

Figure 5:
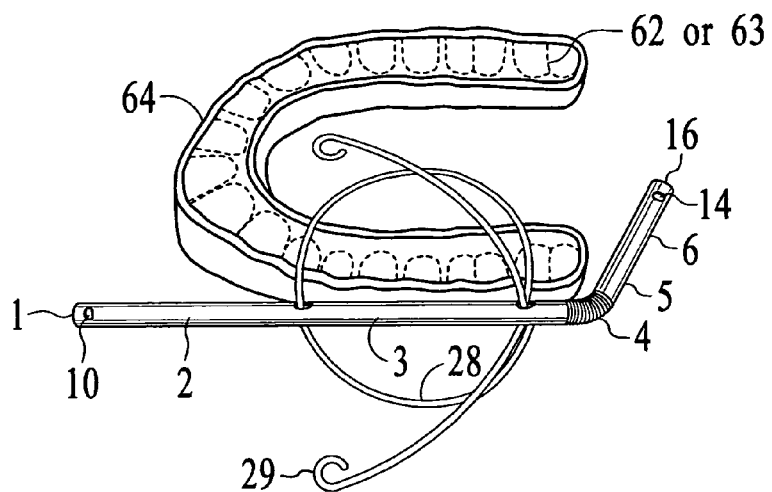
FIG. 5 is a perspective view of a cheek path airway and cheek pouch anchor approximately positioned relative to a dental device.

FIG. 5 depicts a cheek path airway approximately positioned about a dental device 64 which has a channel 62 to engage a user's lower teeth (or 63 if engaging user's upper teeth). The dental device 64 can be used to expand a user's rear-jaw gap, while also performing other functions such as an anti-bruxing device.

Figure 6:
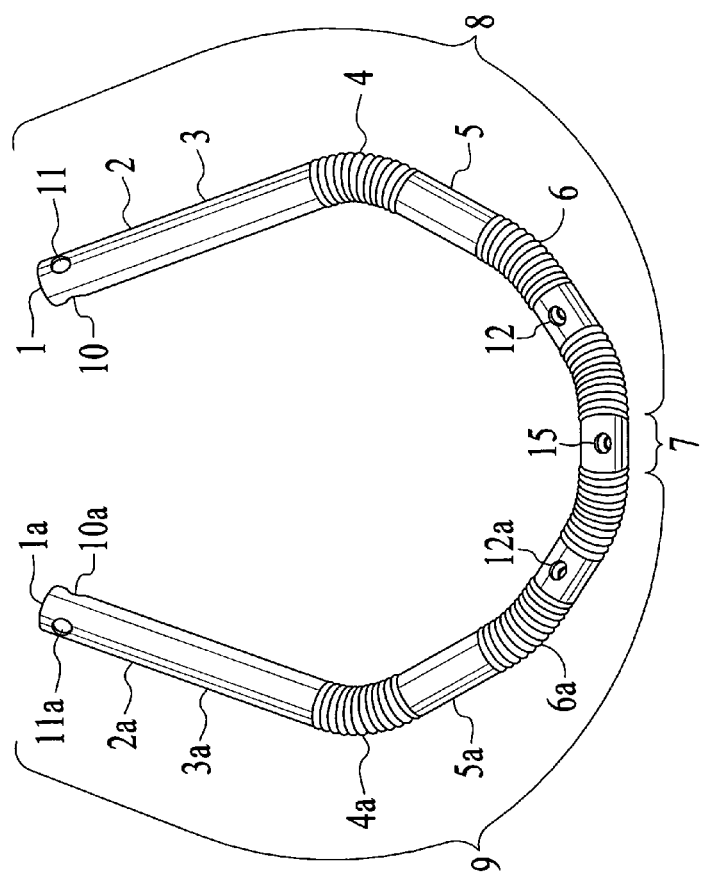
FIG. 6 is a perspective view of a dual cheek path airway folded into the approximate shape for placement in a user's cheek pathways.
Figure 7:
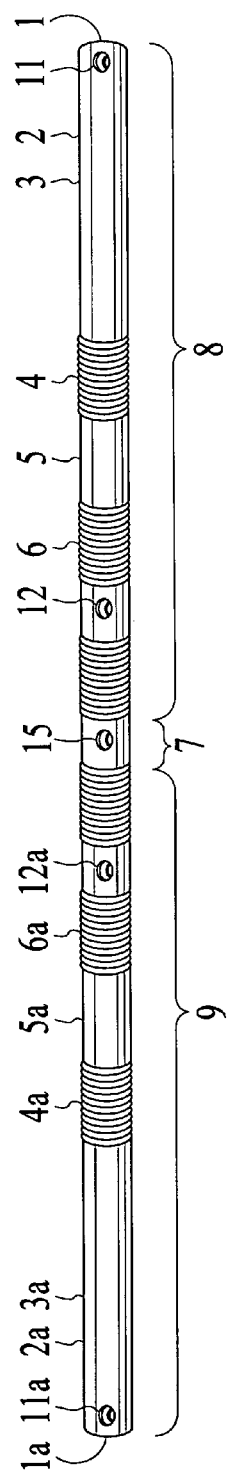
FIG. 7 is a view of the same dual cheek path airway as in FIG. 6, but showing the airway in-line, with a zero curvature along its longitudinal axis, as manufactured but before folding the airway to fit a user's mouth.

FIGS. 6 and 7 are comparative depictions of the same dual cheek path airway, except that in FIG. 7 the airway's longitudinal axis has approximately zero curvature, as manufactured in-line. By comparison, in FIG. 6 the airway has been folded after manufacture to approximate the shape necessary to fit into the cheek pathways in a user's mouth. FIGS. 6 and 7 show a hollow tube having external open end 1 and adjacent air flow openings 10 and 11 in the tube wall; lip portion 2; cheek-side portion 3; rear-tooth corner portion 4; rear-jaw gap portion 5; tongue portion 6 with flexible joints and with air flow opening 12 in the tube wall; and rear-mouth-cavity spanning portion 7 with air flow opening 15 in the tube wall. In the dual cheek path airway the rear-mouth-cavity spanning portion 7 joins first cheek-side portion 8 (comprised of portions 1 through 6) with second cheek-side portion 9 (comprised of portions 1a through 6a).

Figure 8:
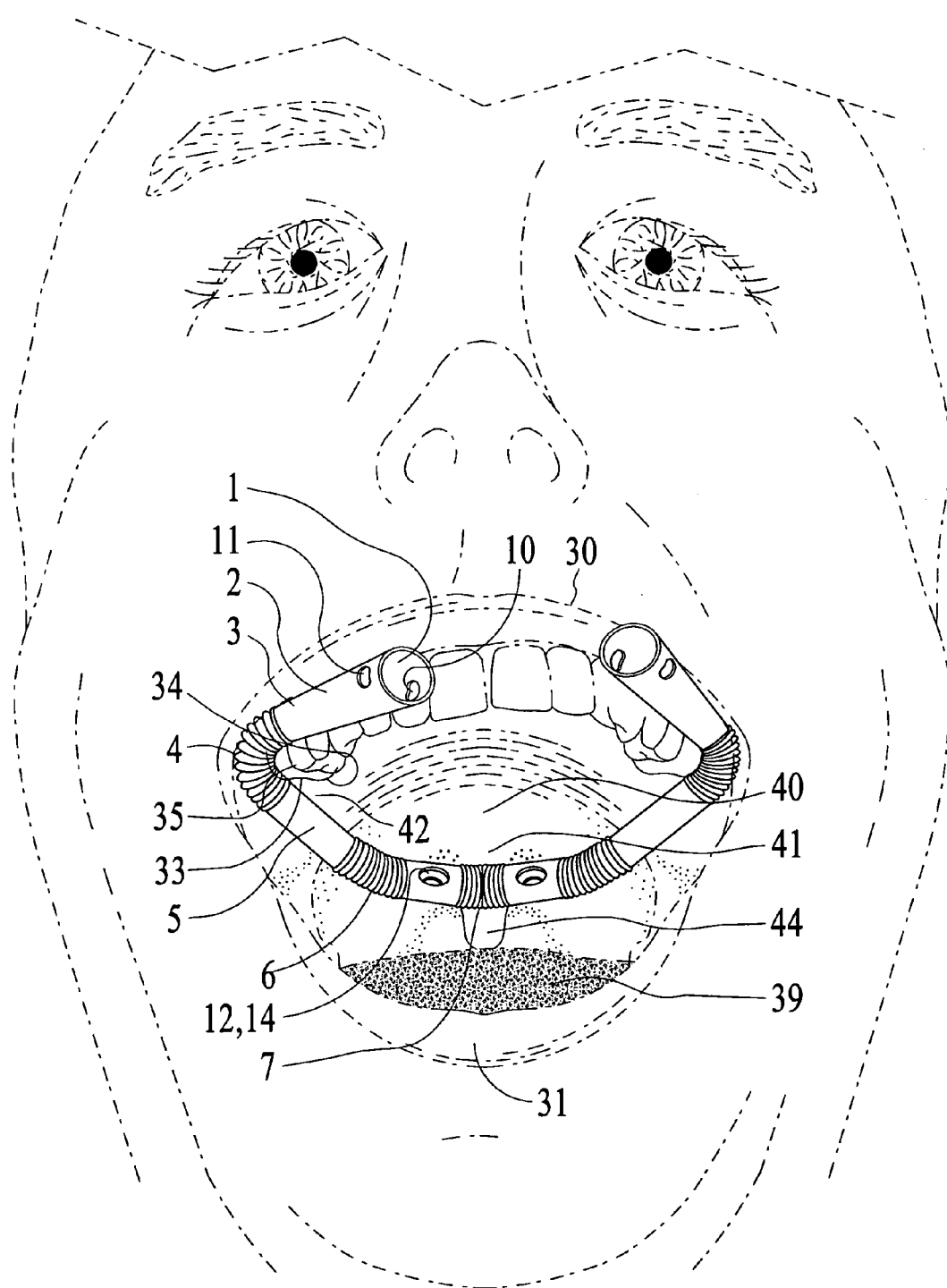
FIG. 8 is a perspective view of a dual cheek path airway placed in cheek pathways in a user's mouth.

FIG. 8 depicts a user's gaping mouth with a dual cheek path airway approximately placed. The view looks at a slight upward angle towards the user's upper teeth including rear-most tooth 33 having lingual side 34 and buccal side 35 with rear-tooth corner portion 4 curved about rear-most tooth 33. FIG. 8 depicts rear-jaw portion 5 of the airway passing through the user's rear-jaw gap 42. It also depicts airway portions 6 and 7, with air flow openings 12 and 14 positioned above the user's tongue 39, in the airspace 41 of the user's rear-mouth cavity adjacent the roof 40 of the user's mouth, ventrally of the user's uvula 44. The depicted placement of the cheek path airway is somewhat distorted, relative to the user's mouth parts, from where the airway would typically lie when the user's mouth is in a less gaping position.

Figure 9:
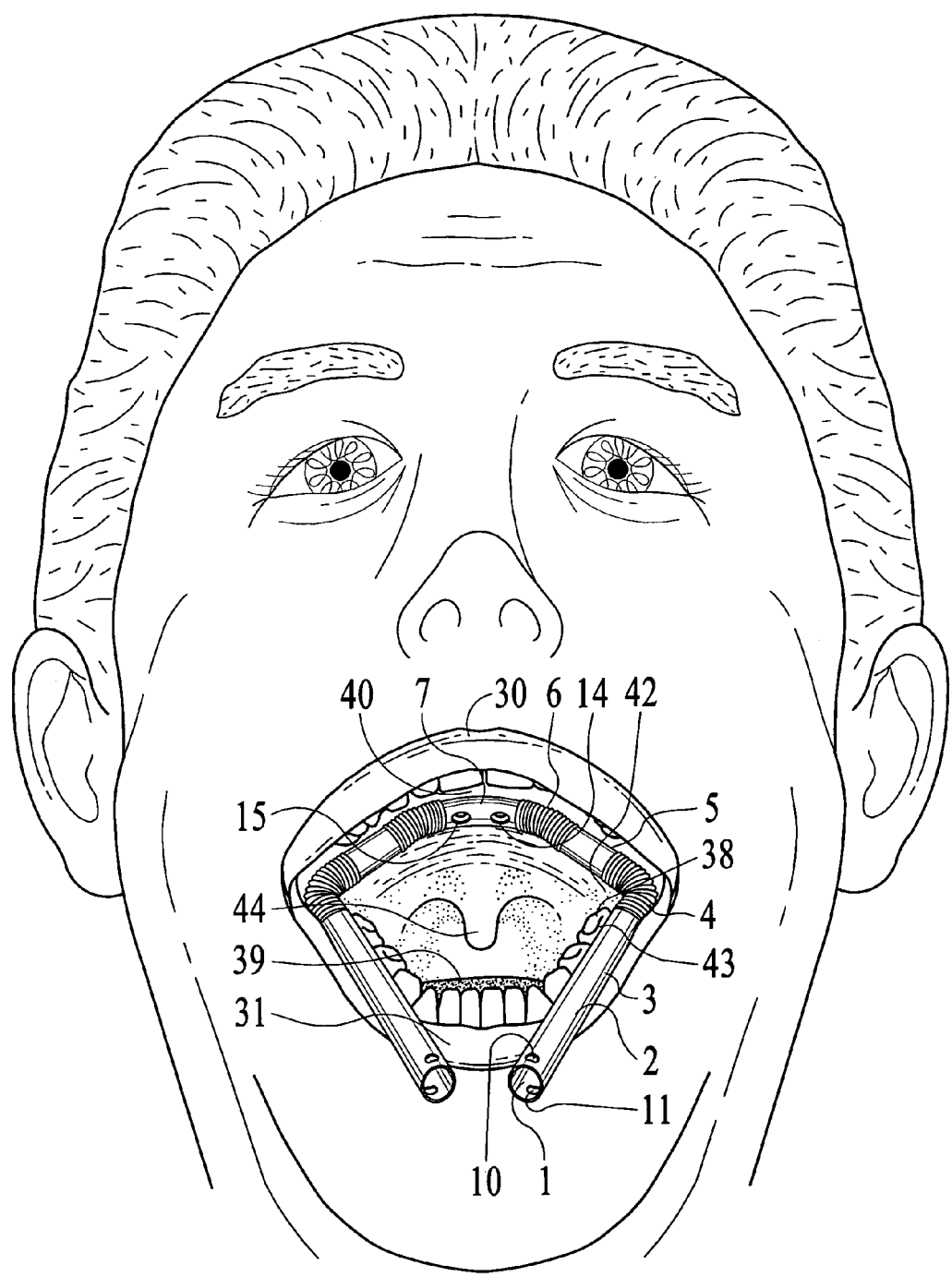
FIG. 9 is a second perspective view of a dual cheek path airway placed in cheek pathways in a user's mouth.

FIG. 9 is the same as FIG. 8 except that the view is at a slightly more downward angle enabling a view of the user's lower teeth and a less obstructed view of the rear of the user's mouth, including uvula 44. This view also somewhat distorts the positioning which the airway would have relative to the user's mouth parts if the user's mouth were in a less gaping posture.

Figure 10:
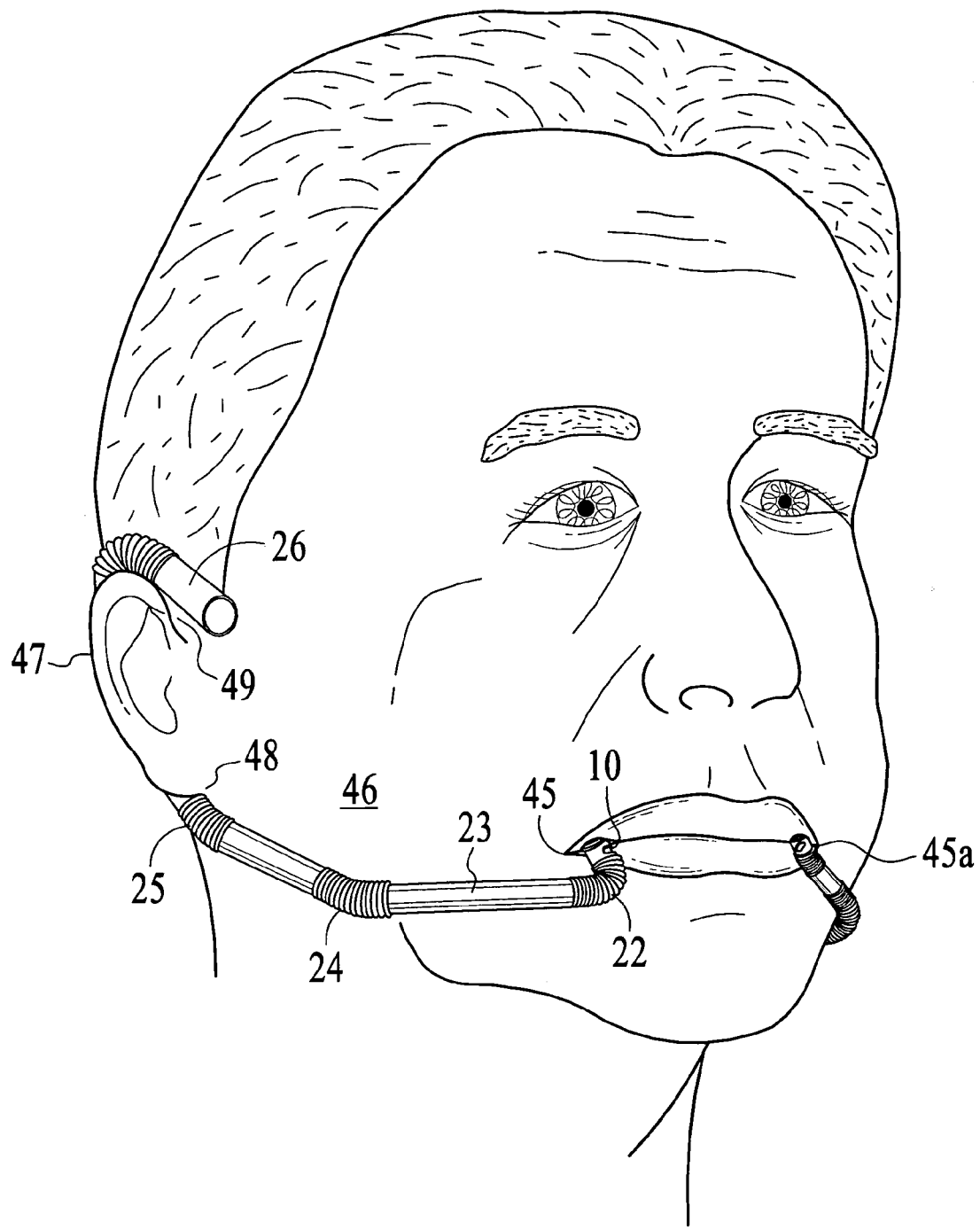
FIG. 10 is an elevation view of a user's face showing external airway stabilizing devices in place.

FIG. 10 shows a front and side perspective view of a user's face with a dual cheek path airway in place and the user's lips closed. The airway projects out through the user's lips, near the corners 45 and 45a of the user's mouth, with external air flow opening 10 adjacent to the user's lips. The second type of retainer, mouth-corner portion 22 of the hollow tube, curves about the corner 45 of the user's mouth. External cheek-side extension 23, having flexible joint portion 24, lies along the outside of the user's cheek 46. Flexible ear piece 25 is curved about the lower side 48 and the upper side 49 of the user's ear 47, and the airway's ear piece 25 terminates in finger grip portion 26.

Figure 11:
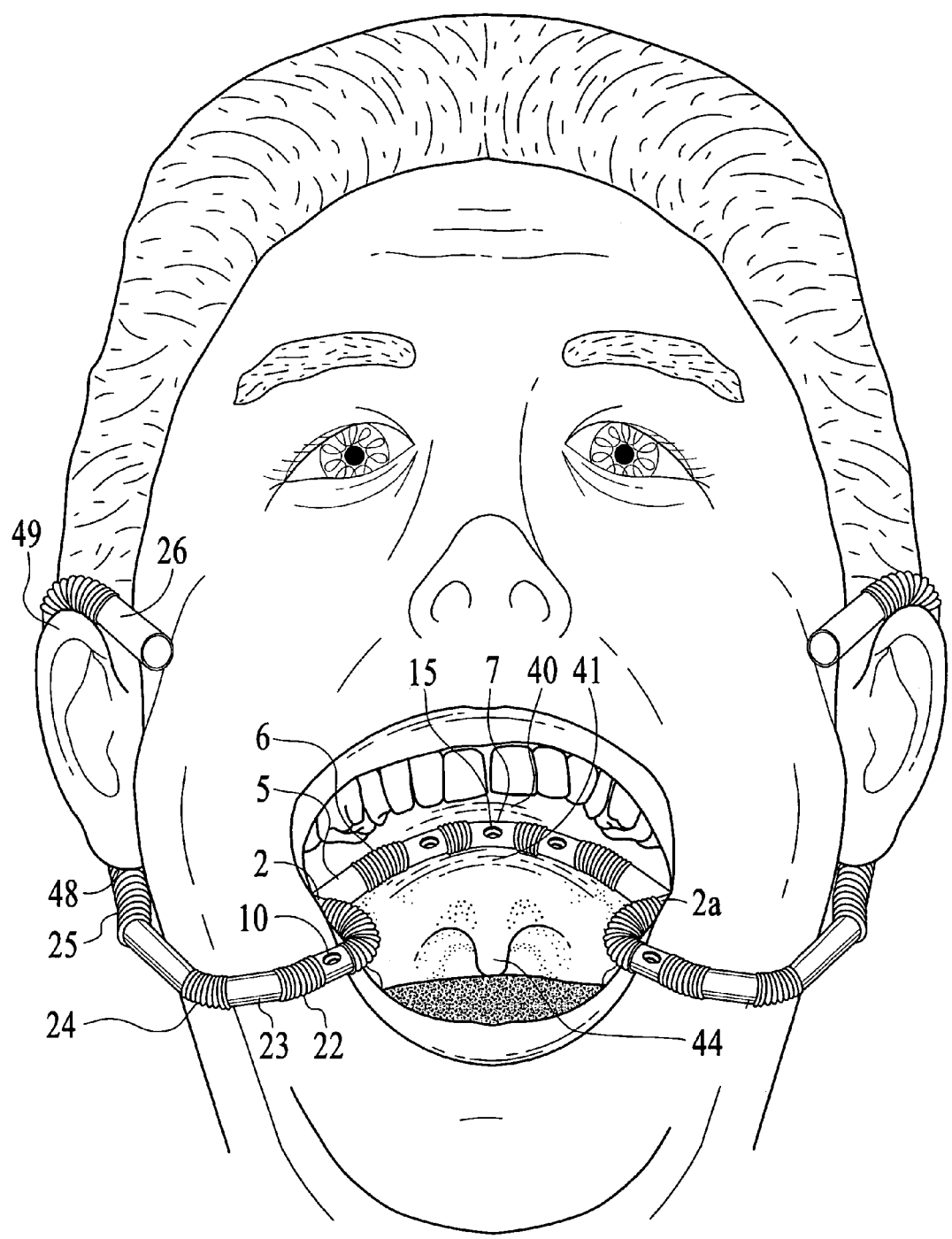
FIG. 11 is a perspective view of a user's face with mouth open, showing a dual cheek path airway with external stabilizing extensions in place.

FIG. 11 depicts a user's face and open mouth with a dual cheek airway in place, where the airway has external stabilizing parts, including mouth-corner portion 22, external cheek-side extension 23 with flexible joint 24, and ear piece 25 with finger grip portion 26.

Figure 12:
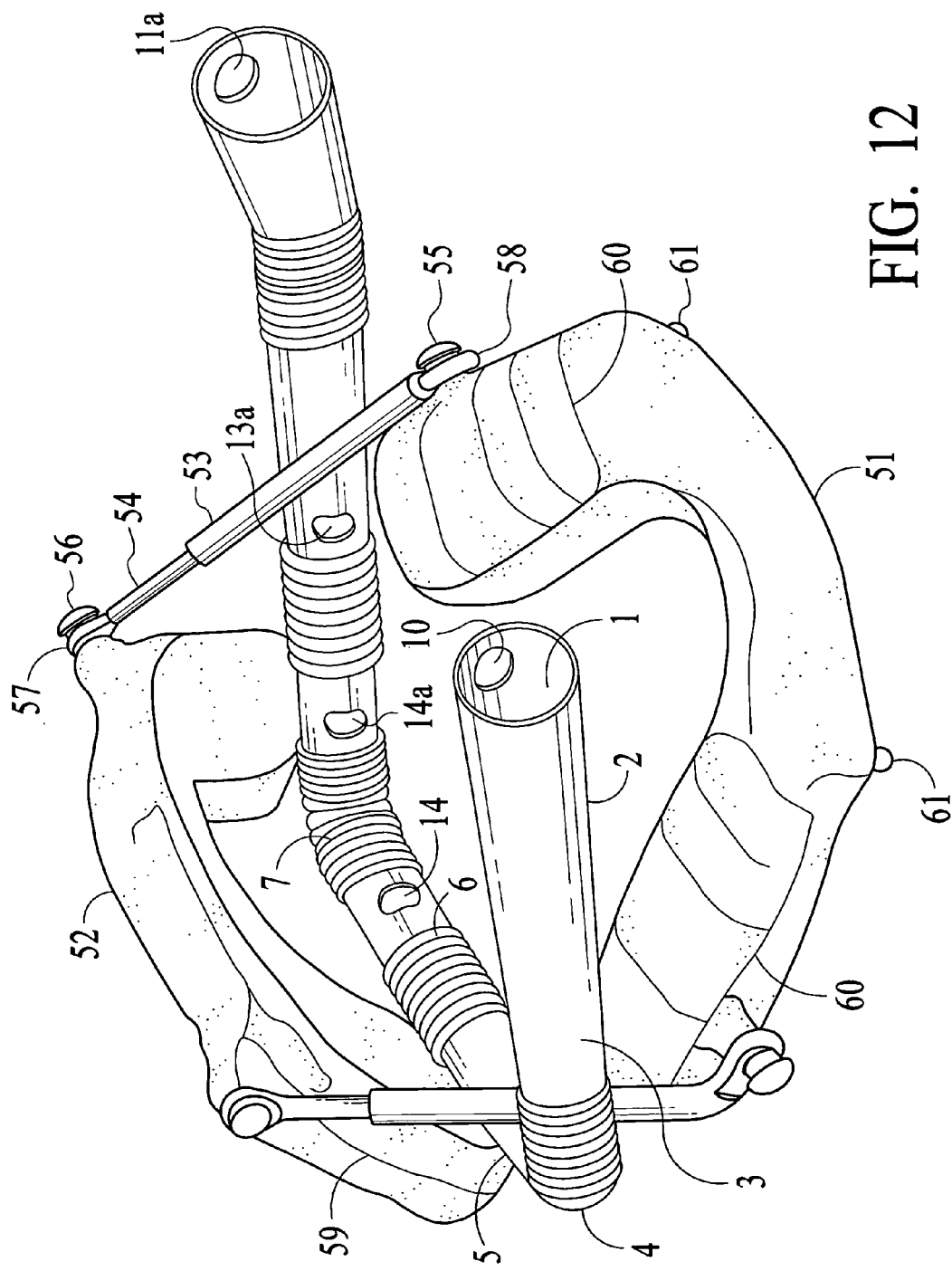
FIG. 12 is a perspective view, from the upper left front, of a dual cheek path airway approximately positioned about an inverted (upside down), articulated, dental jaw-control device.

FIG. 12 depicts a frontal and side perspective view of a dual cheek path airway folded about a dental jaw-control device in a very rough approximation of the relationship that the airway would have to the dental device in a user's mouth, with the airway passing behind the dental device and around the outside of the struts of the dental device. For convenience the dental device is depicted upside down and is articulated to better display its parts. The dental device has a mandibular (lower jaw) portion 52 and a maxillary (upper jaw) portion 51, which are connected by adjustable struts on either side. The struts have female (sleeve) portion 53 which slidably receives male (arm) portion 54. The struts have collars 57 and 58 which are rotatably mounted on pivot bolts 55 and 56. Pivot bolt 55 is rigidly mounted near the dorsal end of maxillary portion 51, and pivot bolt 56 is rigidly mounted near the ventral end of mandibular portion 52. Mandibular portion 52 and maxillary portion 51 typically are formed of plastic cast in molds imprinted by a user's mandibular and maxillary teeth. Wire reinforcing frames 59 and 60, as well as seats for pivot bolts 55 and 56, are embedded in the plastic casts which form mandibular portion 52 and maxillary portion 51. The embedded reinforcing wire frames 59 and 60 are visible because the plastic in which they are embedded is clear. FIG. 12 depicts the dual cheek path airway with flexible rear-tooth corner portion 4 of the airway folded to project cheek-side portion 3 around the outside of the strut of the dental device, and to project rear-jaw-gap portion 5 of the airway about the dorsal corner of the dental device. Flexible joints in tongue portion 6 and rear-mouth-cavity spanning portion 7 of the airway curve about the dorsal side of the dental device.

Figure 13:
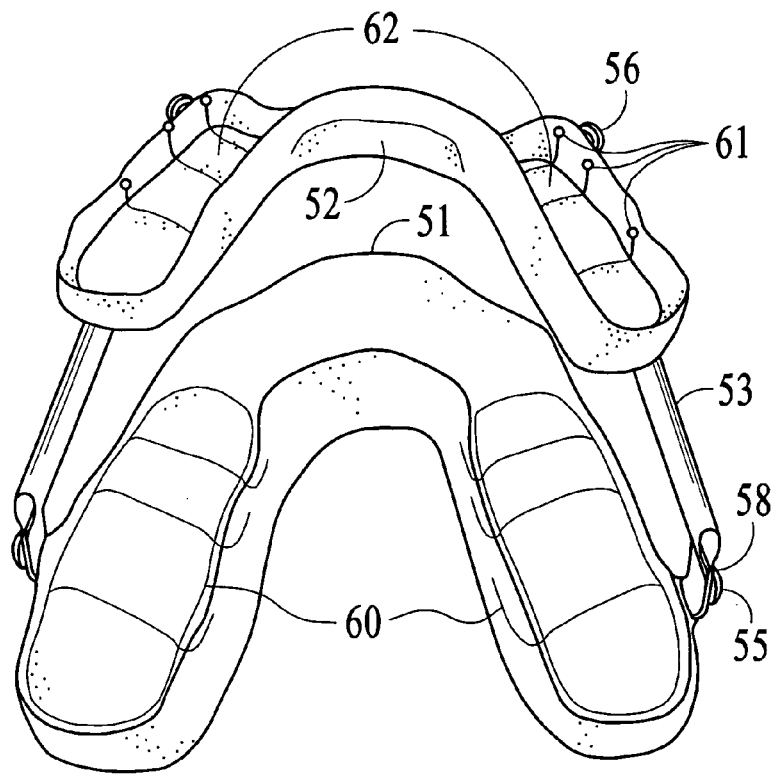
FIG. 13 is a perspective view, from the upper rear, of an articulated, prior art, dental jaw-control device.

FIG. 13 depicts from a dorsal perspective the same dental jaw-control device as that depicted in FIGS. 12 and 13 in combination with cheek path airways. The dental device is depicted upside down to expose the teeth-engaging channel 62 of mandibular portion 52 which is cast from a mold of a user's mandibular teeth. The embedded wire reinforcing frame projects a series of teeth-engaging balls 61 out of the plastic cast adjacent to the buccal wall of teeth-engaging channel 62. FIG. 13 also depicts another view of the wire reinforcing frame 60 embedded in the clear plastic cast which forms maxillary portion 51 of the dental device. The entire dental jaw-control device depicted in FIG. 13 is prior art, but is depicted in order to show additional aspects of the dental device with which the cheek path airway can be combined.

Figure 14:
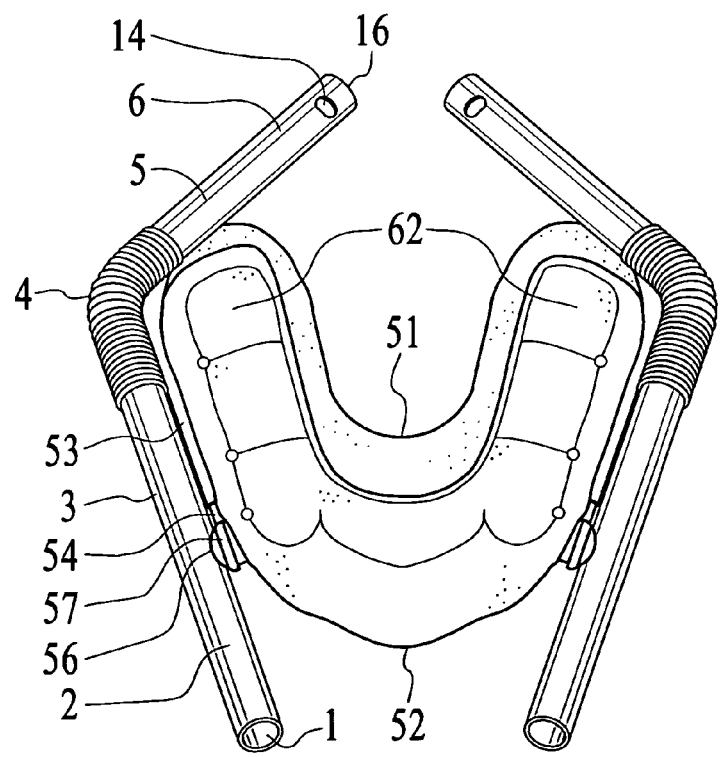
FIG. 14 is a plan view of an inverted (upside down) dental jaw-control device with two single-cheek versions of the airway approximately positioned about it.

FIG. 14 is a plan view depicting two single-cheek versions of the airway approximately positioned about the same dental jaw-control device as is depicted in FIGS. 12 and 13. FIG. 14 shows rear-tooth corner portion 4 of the airway flexed about the dorsal corner of the dental device, projecting rear-jaw gap portion 5 and tongue portion 6 of the airway about the dorsal side of the dental device and projecting cheek-side portion 3 around the outside of the struts of the dental device, in approximately the positions which the airways would have relative to the dental device when both are in place in a user's mouth with the user's jaws closed.

Figure 15A:
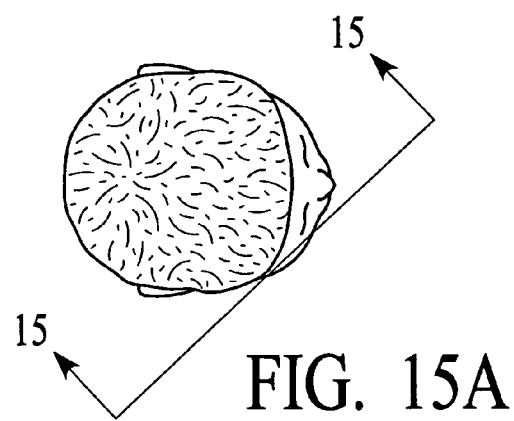
FIG. 15 is an elevation view of the side of a user's face, showing a section view along section 15-15 of FIG. 15A with the user's cheek removed, and showing a cheek path airway placed about a dental jaw-control device in the user's mouth.
Figure 15:
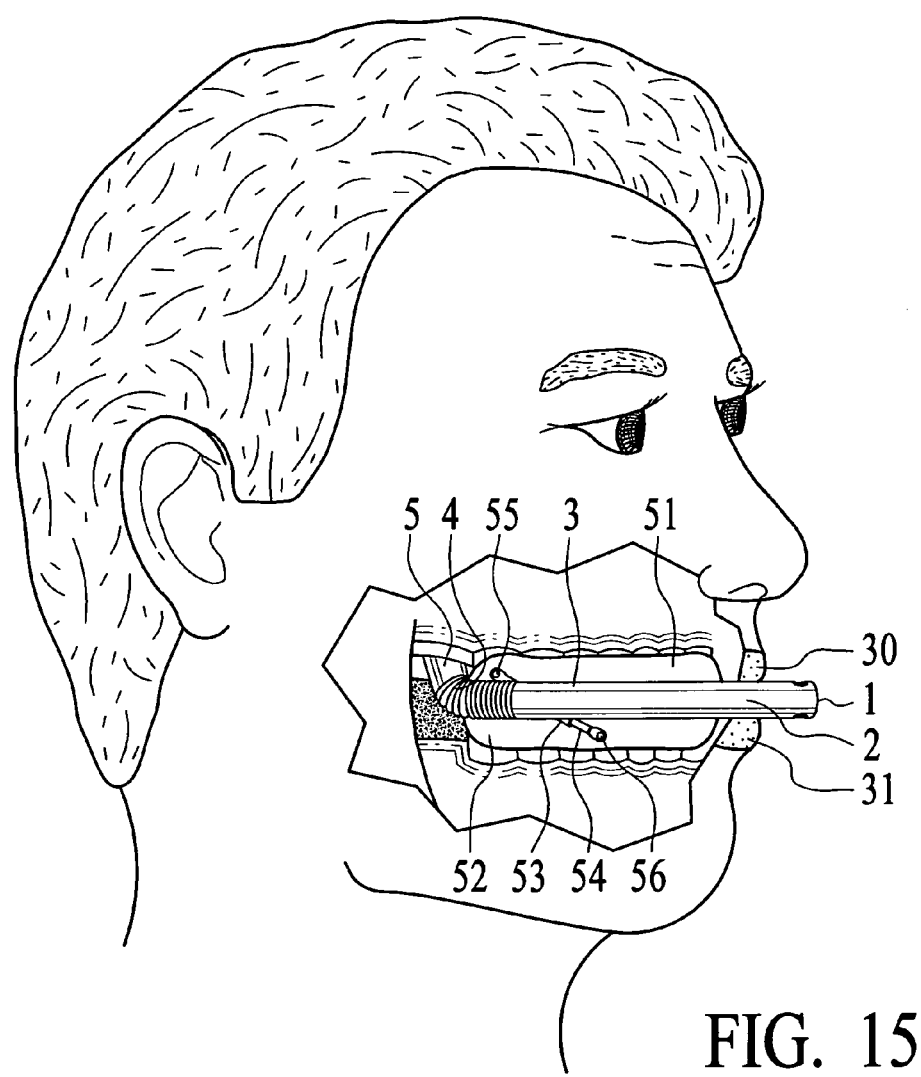

FIG. 15 is a side view of a user's face, along section 15-15 of FIG. 15A, with the user's cheek removed. It shows a cheek path airway placed in a user's cheek pathway so as to operate cooperatively with a dental jaw-control device which also is in place in the user's mouth. Maxillary portion 51 of the dental device is engaging the user's maxillary teeth and mandibular portion 52 is engaging the user's mandibular teeth, with pivot bolt 56 disposed more ventrally on mandibular portion 52 and pivot bolt 55 disposed more dorsally on maxillary portion 51 so that the user's mandibular jaw is urged ventrally relative to the user's maxillary jaw. The purpose is to prevent the user's mandibular jaw from sagging dorsally towards the user's throat when the user is lying more or less supine during sleep. The dental device also can serve an anti-bruxing function. A cheek path airway is placed around the dental device with cheek-side portion 3 of the airway positioned outside the strut (sleeve 53 and arm 54) of the dental device. The rear-tooth corner portion 4 of the airway curves about the dorsal corner of the dental device, and rear-jaw gap portion 5 of the airway projects dorsally of the dental device. In this configuration the user can open and close the user's jaws, operating the slidable sleeve 53 and arm 54 of the dental device while the collars of the strut rotate about pivot bolts 55 and 56. When placed in a cheek pathway the inner wall of the user's cheek (not shown in FIG. 15) drapes over and presses against the relatively rigid cheek-side portion 3 of the airway while the relatively rigid lip portion 2 of the airway projects between the user's lips 30 and 31. Pressure of the user's inner cheek wall and mouth corner (not shown in FIG. 15) urges portion 3 of the airway against the strut (sleeve 53 and arm 54) of the dental device, helping constrain pitch and yaw rotation of the airway. Sleeve 53 and arm 54 of the dental device also prevent cheek-side portion 3 of the airway from slipping laterally between the maxillary and mandibular portions 51 and 52 of the dental device when the user's jaws open.

PREFERRED EMBODIMENTS OF INVENTION

Airway Tube. In a preferred version, the cheek path airway is formed as a relatively rigid tube with flexible joints interspersed at strategic positions along the tube's longitudinal axis. The more rigid sections of the tube provide structural stability and better leverage to avoid the biting surfaces of a user's teeth, as well as to better project the internal and external open ends of the airway into desirable locations. By reference to FIGS. 3, 4, 8, 9, 10, 11 and 15, the user's inner cheek wall drapes over and provides cheek-side pressure upon cheek-side portion 3 which is relatively rigid along the longitudinal axis. In FIGS. 3, 3A, 8, 9, 10, 11, 15 and 15A the user's inner cheek walls are not visible and labeled but may be inferred from human anatomy. The user's mouth corners 45 and 45A, labeled in FIG. 10, and the user's lips 30 and 31 can drape about airway portions 2 and 2A as depicted in FIGS. 3, 8, 9, 10, 11 and 15. FIG. 4, a schematic, is not drawn to scale but rather exaggerates spacing between the user's inner cheek walls 32 and 32A and airway cheekside portions 3 and 3A in order to more clearly delineate the airway structure from the user's mouth tissues. By reference to FIG. 15 the draping effect of the user's cheek (not shown) urges cheek-side portion 3 against sleeve 53 and arm 54 of the strut of the dental device, constraining rear-tooth corner portion 4 and rear-jaw gap portion 5 of the tube from yawing into the inter occlusal space between mandibular portion 52 and maxillary portion 51 of the dental device. By reference to FIG. 3, the draping effect of the user's cheek (not shown) presses against both rigid cheek-side portion of the airway and against the cheek pouch anchor, again constraining yawing of rear-tooth corner portion 4 and rear-jaw gap portion 5.

In-Line Manufacture of Airway Tube. The airway tube, including the flexible joints, preferably is manufactured "in-line," that is, with near-zero curvature in the longitudinal axis of the tube, as in FIGS. 1 and 7. Such near-zero curvature during manufacture will ease manufacture, packaging, transportation, storage and retail display of the airway, while the interspersed flexible joints enable a user to shape the tube along its longitudinal axis to fit the user's mouth, as in FIGS. 1, 6 and 8-11.

A modification of the instant cheek airway is designed to enable incorporation of a mouth-corner retainer element in a single, in-line manufacturing process by simply extending the length of the hollow tube with flexible joints inserted to enable the tube to fold about the corner of a user's mouth and along the outer wall of a user's cheek, depicted as element 22 in FIGS. 4, 10 and 11. The tube can even be manufactured in-line with sufficient length to curve about a user's ears, as element 25 in FIGS. 10 and 11. Adaptation of the hollow tube for in-line manufacturing is preferred to eliminate the necessity to add flanges by some additional assembly process, and has the added features of easier packing, shipping and display, while enabling the end user to fold the in-line tube for better personal fit.

Tongue-Avoiding Feature. In one preferred modification of the cheek airway invention, at least one of the rear-tooth corner portion 4, the rear-jaw gap portion 5 and the tongue portion 6 of the airway is stiffly flexible so that a user's tongue can press the airway into locations of lesser interference with the user's tongue, near the side and roof of the user's rear-mouth cavity. Not only does the resulting configuration reduce interference with the user's tongue, but also it can help retain the airway in the user's cheek pathway.

Tube Diameters Related to Rear-jaw Gap and Lip Seal. By comparison to the 2 to 3 mm inside diameter which is explicitly disclosed for the pressure-equalization conduit of Pope, et al., U.S. Pat. No. 4,553,549, larger diameters are preferred for the instant invention, to the extent that the user's rear-jaw gap can accept such larger diameters; larger diameters enable the higher flow volumes desired for the breath-supplementation function of the instant invention. By way of non-limiting example, tube inside diameters of approximately 5.5 mm to 6.5 mm, have been used in the instant invention for an adult human. The instant invention is not specifically limited to such range of diameters, but rather it typically will be limited by the cross-sectional area of the particular user's rear-jaw gap.

Lip-sealing problems can be mitigated in the instant invention by employing a smaller diameter tube around which a user's lips still can nearly seal. When using such smaller diameter tubes, one accepts that the resulting lesser air flow through the cheek path airway may only supplement, not entirely replace, nasal breathing. However, lip sealing tends to be a less critical issue in the instant invention because the invention is founded in part upon a recognition that there can be benefit to preservation of some nasal air flow by using a cheek path airway merely to supplement nasal air flow rather than replacing it; as a result a tube smaller than the diameter tube required to completely replace nasal breathing can be employed to more readily allow the user's lips to seal about the tube.

In many instances the maximum radial cross-section of a tube which can be fitted to a user's rear-jaw gap also will be small enough to allow the a user's lips to seal around the instant cheek airway tube sufficiently to render lip sealing an insignificant issue. While it is desirable in the instant invention to preserve a user's normal lip seal when the user is breathing nasally, the instant invention is designed to not prevent and not hinder open-mouth breathing when the user's physiologic state naturally triggers a switch from nasal to open-mouth breathing. When supplementing nasal air flow, the instant invention does not necessarily require a strict lip seal, but it is desirable to enable a user to substantially preserve the user's natural lip seal.

Methods of Making and Using.

The cheek path airway can be manufactured from plastic materials such as those in use for flexible drinking straws, provided that they be essentially non-toxic. It is conceived that the cheek path airway could be manufactured by modification of methods and machines presently widely used for the manufacture of flexible drinking straws.

Portions of a relatively rigid tube can be rendered flexible by imposing corrugations in the tube wall similar to those which render plastic drinking straws flexible. Such corrugations can render a tube somewhat extensible as well as flexible. A wide variety of methods could impart the essential curves to fit a user's cheek path. For example, portions of the tube could be rendered flexible by helical coils of wire or filament covered by an outer sheath; or semi-rigid, semi-flexible tubing could be used throughout and adjusted by hand molding to fit a cheek pathway. Materials of differing flexibility could be fused or welded together. The degree of flexibility versus rigidity could be altered by controlling the thickness of the tube walls and their chemical composition.

The thickness of the walls of plastic tubes can be adjusted to enable such tube walls to deform to a flattened or oval shape, which better conforms to the cross-section of a particular user's rear-jaw gap, but without collapse of the hollow air passageway. The deformation can be flexible or malleable, as well as resilient. For comfortable fit, it is preferable that the outer surface of the rear-jaw gap portion 5 of the airway tube be smooth, rather than corrugated, to minimize irritation when the jaws close the rear-jaw gap to its minimum cross-section.

Airflow openings and filament-lacing holes can be melted through the walls of plastic tubes by use of a heated pointed instrument. It is conceived that the tube walls could be initially formed with such openings, or openings could be cut or stamped, or formed with a focused laser beam.

It is conceived that in a combination of the cheek pouch anchor with the cheek path airway, much of the stabilizing function can be assumed by the anchor, permitting a wider range in the design of flexibility and rigidity in the tube.

The filament used in the cheek pouch anchor can be manufactured from monofilament plastic line similar to that in common use for heavier weights of fishing line, provided that it be essentially non-toxic. Flexibility and resilience can be controlled by controlling the size of the cross-section of the monofilament, as well as its composition. It is conceived that flexibility and resilience also could be affected by changes in the shape of the monofilament's cross-section. Such monofilament line can be heat-molded at relatively low temperatures into curves of the desired shapes and it develops a "memory" for such a heat-molded shape which aids shaping of spring-like curves in the monofilament line. Altering the locations of the lacing holes 17 in portion 3 of the airway tube alters the shape of the curves in the cheek pocket anchor. The filament could be formed or metal or a combination of metal and plastic.

The cheek path airway, the cheek pouch anchor, and the combination of them, can be sanitized in an ordinary household dishwasher in the same manner as dining utensils, provided that temperatures in the machine are not so high as to excessively soften the materials of the devices.

Because all parts can be formed of plastic, it is conceived that the cheek path airway, and possibly the combination of the cheek path airway and cheek pouch anchor, could be manufactured and assembled sufficiently inexpensively for short term use and possibly to be disposable.

Some Definitions Used in the Claims.

For purposes of the claims the following words have the following meanings:

"Conduit" means a hollow tube or channel capable of conveying fluids along its longitudinal axis, which axis may be curved. A conduit may have one or more separate passageways through it and thus have a plurality of longitudinal axial dimensions. The conduit's cross-section may enclosed (as in a tube by way of non-limiting example), or partially open (as in an open-top channel by way of non-limiting example). The conduit's radial cross-section may have a single-focus radius (circular cross-section) or may have multi-focal radii or variable length radii and thus have a plurality of radial dimensions (oval or other variant shape which can include multi-lateral shapes, that is, a plurality of sides). A conduit's radial cross-section may vary along the conduit's longitudinal axis.

"Curve" means a geometric figure which may have any degree of curvature; it may but need not include zero curvature, that is, a straight line, as well as positive or negative curvature.

"Filament" includes at least one thread, fibre, strand, wire, line, string, strip, or the like. It may include multi-strand or braided configurations. The radial cross-section of the filament may, but need not necessarily be, circular.

"Flexible" includes bendable, pliable, moldable, and adjustable.

"Portion" of a conduit refers to an approximate functional location or position along the longitudinal axis of the conduit, without necessarily implying sharp or distinct boundaries between portions and functions; one portion may have an indistinct or blended joinder with another portion, and when the conduit is installed in a user's mouth a portion may conform only approximately to the indicated parts of a user's mouth.

I claim:

1. A cheek pouch anchor, for placement within a user's cheek pouch to maintain positioning of a work piece in a user's mouth while a user's jaws, inter occlusal space, and lips open and close, comprising:
    a spring element adapted to be placed within a user's cheek pouch, and to compress as a user's jaws close, and
        to resiliently expand so as to form and maintain a span bridging across a user's inter occlusal space and a user's lip opening formed as a user's jaws and lips open and close, and
        to receive joinder to a work piece, and
    having structural strength sufficient, when joined to a work piece, to maintain placement within a user's cheek pouch while a user's lips and jaws open and close, wherein said spring element further comprises:
    said cheek pouch anchor is joined with a conduit for a fluid, which conduit is adapted for placement at least partially in a user's cheek pouch.

2. The cheek pouch anchor of claim 1 further comprising:
    said fluid conduit has a conduit wall,
    said conduit wall has at least one hole, and
    said cheek pouch anchor is joined to said fluid conduit by lacing the spring element of said cheek pouch anchor through at least one hole in said conduit wall.

3. A cheek pouch anchor, for placement within a user's cheek pouch to maintain positioning of a work piece in a user's mouth while a user's jaws, inter occlusal space, and lips open and close, comprising:
    a spring element adapted to be placed within a user's cheek pouch, and
        to compress as a user's jaws close, and
        to resiliently expand so as to form and maintain a span bridging across a user's inter occlusal space and a user's lip opening formed as a user's jaws and lips open and close, and
        to receive joinder to a work piece, and
    having structural strength sufficient, when joined to a work piece, to maintain placement within a user's cheek pouch while a user's lips and jaws open and close, wherein said spring element further comprises:
    a resilient filament
        which is configured into a plurality of connected loops, each loop having a loop span size, and
        said plurality of loops are combined to form a whole spring element with a whole spring element span size, and
        each one of said plurality of loop span sizes is mutually adjustable relative to at least one other of said loop span sizes, such that an increase or decrease in the loop span size of any one of said plurality of loops results in a converse decrease or increase in the loop span size of at least one other of said plurality of loops, thereby enabling adjustment of said whole spring element span size by said mutual adjustment within said plurality of loop span sizes.

4. An adjustable cheek pouch anchor, for placement within a user's cheek pouch to maintain positioning of a work piece in a user's mouth while a user's jaws, inter occlusal space, and lips open and close, comprising:
    a spring element formed of a resilient filament
        sized to fit within a user's cheek pouch, and
        having a dynamic span
            that is resiliently expandable within a user's cheek pouch to maintain a bridge across a user's inter occlusal space and lip opening that form as a user's jaws open, and
            that is flexibly compressible to allow a user's jaws and lips to fully close while said spring element is within a user's cheek pouch, and
        capable of receiving attachment of a work piece, and having structural strength that is sufficient for said spring element to maintain itself, with a work piece attached to it, within a user's cheek pouch while a user's jaws open and close; and
    said resilient filament
        is configured into a plurality of connected loops
            each such loop having a loop span size, and
            each such loop span size having a range of expansion and compression, and
        said plurality of connected loops form a whole spring element having a whole spring element span size, and
            said whole spring element span size having a range of expansion and compression, and
            said range of expansion and compression of least one of said loop span sizes of said plurality of connected loops is adjustable relative to at least one other of said loop span sizes, and
            said connected loops translate an adjustment in said range of expansion and compression of the loop span size of at least one of said plurality of connected loops into an adjustment in said range of expansion and compression of said whole spring element span size.

5. A cheek pouch anchor, for placement within a user's cheek pouch to stabilize a work piece in a user's mouth, comprising:
    a spring element sized to fit within one of a user's cheek pouches, and having a dynamic span such that said spring element resiliently expands within one or more of a user's cheek pouches to maintain a bridge across a user's inter occlusal space and lip opening that form as a user's jaws open, and said spring element flexibly compresses to allow a user's jaws and lips to fully close while said spring element is within one or more of a user's cheek pouches, and having the capability to receive attachment to a work piece, and having structural strength that is sufficient for said spring element, with a work piece attached, to maintain itself within one or more of a user's cheek pouches while a user's jaws open and close, further comprising:

said cheek pouch anchor is joined with a conduit for a fluid, which conduit is configured to enable placement of it at least partially in one or more of a user's cheek pouches.

* * * * *